US012009675B2

United States Patent
Lyu et al.

(10) Patent No.: US 12,009,675 B2
(45) Date of Patent: Jun. 11, 2024

(54) APPARATUS AND METHODS FOR REAL-TIME RESONANCE ADAPTATION FOR POWER RECEIVER

(71) Applicant: The Regents of the University of California, Oakland, CA (US)

(72) Inventors: Hongming Lyu, Shanghai (CN); Aydin Babakhani, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 2 days.

(21) Appl. No.: 18/048,333

(22) Filed: Oct. 20, 2022

(65) Prior Publication Data
US 2023/0216347 A1 Jul. 6, 2023

Related U.S. Application Data

(63) Continuation of application No. PCT/US2021/024888, filed on Mar. 30, 2021.

(60) Provisional application No. 63/013,797, filed on Apr. 22, 2020.

(51) Int. Cl.
| | | |
|---|---|---|
| H02J 50/12 | (2016.01) | |
| H02J 50/00 | (2016.01) | |
| H02J 50/20 | (2016.01) | |
| H02J 50/80 | (2016.01) | |
| A61N 1/378 | (2006.01) | |
| H04B 1/7163 | (2011.01) | |

(52) U.S. Cl.
CPC ............ *H02J 50/12* (2016.02); *H02J 50/005* (2020.01); *H02J 50/20* (2016.02); *H02J 50/80* (2016.02); *A61N 1/3787* (2013.01); *H02J 2310/23* (2020.01); *H04B 1/71635* (2013.01)

(58) Field of Classification Search
CPC ...................................................... H02J 50/12
USPC ........................................................ 307/104
See application file for complete search history.

(56) References Cited

U.S. PATENT DOCUMENTS

| | | | | |
|---|---|---|---|---|
| 7,719,416 B2 * | 5/2010 | Arms | ................... | B64C 27/006 702/33 |
| 10,498,160 B2 * | 12/2019 | Desai | ..................... | H02J 50/12 |
| 2006/0281435 A1 * | 12/2006 | Shearer | ............. | G06K 19/0702 455/343.1 |

(Continued)

FOREIGN PATENT DOCUMENTS

| | | |
|---|---|---|
| EP | 4138987 A1 | 3/2023 |
| JP | 2023523717 A | 6/2023 |
| WO | 2021216256 A1 | 10/2021 |

OTHER PUBLICATIONS

International Preliminary Report on Patentability for International Application PCT/US2021/024888, Report issued Oct. 25, 2022, Mailed on Nov. 3, 2022, 10 pgs.

(Continued)

*Primary Examiner* — Joseph Chang
(74) *Attorney, Agent, or Firm* — KPPB LLP

(57) ABSTRACT

Wirelessly powered receiver system and sensors are described. In an embodiment, the power receiver system, includes an inductive coil that receives wireless power from an external transmitter, a capacitor bank that optimizes power transfer to an energy harvesting device, and a power-receiving frontend RF-DC rectifier with a periodically enabled closed feedback loop that adapts settings of the capacitor bank in real-time to adapt to changes on the inductive coil to maximize power transfer efficiency.

27 Claims, 31 Drawing Sheets

(56) References Cited

U.S. PATENT DOCUMENTS

| | | |
|---|---|---|
| 2008/0158028 A1 | 7/2008 | Yang et al. |
| 2009/0102296 A1* | 4/2009 | Greene .................. H01Q 1/243 |
| | | 307/149 |
| 2012/0161529 A1* | 6/2012 | Kamata .................. H02J 50/90 |
| | | 307/104 |
| 2016/0094043 A1* | 3/2016 | Hao ........................ H04B 5/26 |
| | | 307/104 |
| 2016/0276877 A1 | 9/2016 | Weale |
| 2017/0126281 A1 | 5/2017 | Cook et al. |
| 2017/0229921 A1 | 8/2017 | Hwang et al. |
| 2019/0109499 A1* | 4/2019 | Smith .................... H02M 3/156 |
| 2019/0280527 A1 | 9/2019 | Smith et al. |

OTHER PUBLICATIONS

International Search Report and Written Opinion for International Application No. PCT/US2021/024888, Search completed May 26, 2021, Mailed Jun. 8, 2021, 15 pgs.

Abdelhalim et al., "64-channel UWB wireless neural vector analyzer SOC with a closed-loop phase synchrony-triggered neurostimulator", IEEE Journal of Solid-State Circuits, vol. 48, No. 10, 2013, pp. 2494-2510, Oct. 2013, first published Jul. 31, 2013, DOI: 10.1109/JSSC.2013.2272952.

Agarwal et al., "A 4uW, ADPLL-Based Implantable Amperometric Biosensor in 65nm CMOS", 2017 Symposium on VLSI Circuits, Kyoto, Japan, 2017, pp. C108-C109. doi: 10.23919/VLSIC.2017.8008566.

Bourdel et al., "A 9-pJ/Pulse 1.42-Vpp OOK CMOS UWB Pulse Generator for the 3.1—10.6-GHz FCC Band", IEEE Transactions on Microwave Theory and Techniques, vol. 58, No. 1, Jan. 2010, pp. 1-9.

Chae et al., "A 128-Channel 6 mW Wireless Neural Recording IC With Spike Feature Extraction and UWB Transmitter", IEEE Transactions on Neural Systems and Rehabilitation Engineering, vol. 17, No. 4, Aug. 2009, pp. 312-321, DOI: 10.1109/TNSRE.2009.2021607.

Choi et al., "Resonant regulating rectifiers (3R) operating for 6.78 MHz resonant wireless power transfer (RWPT)", IEEE Journal of Solid-State Circuits, vol. 48, No. 12, Dec. 2013, first published Nov. 20, 2013, pp. 2989-3001, DOI: 10.1109/JSSC.2013.2287592.

Cong et al., "A wireless and batteryless 10-bit implantable blood pressure sensing microsystem with adaptive RF powering for real-time laboratory mice monitoring", IEEE Journal of Solid-State Circuits, vol. 44, No. 12, Dec. 15, 2009, pp. 3631-3644, DOI: 10.1109/JSSC.2009.2035551.

Dickson, "On-chip high-voltage generation in MNOS integrated circuits using an improved voltage multiplier technique", IEEE Journal of Solid-State Circuits, vol. 11, No. 3, 1976, pp. 374-378, http://dx.doi.org/10.1109/JSSC.1976.1050739.

Gao et al., "Low-power ultrawideband wireless telemetry transceiver for medical sensor applications", IEEE Transactions on Biomedical Engineering, vol. 58, No. 3, Mar. 2011, pp. 768-772, DOI: 10.1109/TBME.2010.2097262.

Huang et al., "A 13.56-MHz wireless power transfer system with enhanced load-transient response and efficiency by fully integrated wireless constant-idle-time control for biomedical implants", IEEE Journal of Solid-State Circuits, vol. 53, No. 2, Feb. 2018, pp. 538-551, DOI: 10.1109/JSSC.2017.2767181.

Huang et al., "A self-powered CMOS reconfigurable multi-sensor SoC for biomedical applications", IEEE Journal of Solid-State Circuits, vol. 49, No. 4, Apr. 2014, first published Jan. 24, 2014, pp. 851-866, DOI: 10.1109/JSSC.2013.2297392.

Jeon et al., "A Smart Contact Lens Controller IC Supporting Dual-Mode Telemetry With Wireless-Powered Backscattering LSK and EM-Radiated RF Transmission Using a Single-Loop Antenna", IEEE Journal of Solid-State Circuits, vol. 55, No. 4, Apr. 2020, first published Dec. 25, 2019, pp. 856-867, DOI: 10.1109/JSSC.2019.2959493.

Kang et al., "Design and Optimization of Area-Constrained Wirelessly Powered Cmos UWB SoC for localization applications", IEEE Transactions on Microwave Theory and Techniques, Apr. 2016, vol. 64, No. 4, pp. 1042-1054, DOI: 10.1109/TMTT.2016.2536663.

Kim et al., "A 144-MHz Fully Integrated Resonant Regulating Rectifier With Hybrid Pulse Modulation for mm-Sized Implants", IEEE Journal of Solid-State Circuits, vol. 52, Issue 11, Nov. 2017, pp. 3043-3055, DOI: 10.1109/JSSC.2017.2734901.

Lam et al., "Integrated low-loss CMOS active rectifier for wirelessly powered devices", IEEE Transactions on Circuits and Systems II: Express Briefs, vol. 53, No. 12, Dec. 2006, pp. 1378-1382, DOI: 10.1109/TCSII.2006.885400.

Lee et al., "A programmable implantable microstimulator SoC with wireless telemetry: Application in closed-loop endocardial stimulation for cardiac pacemaker", IEEE Transactions on Biomedical Circuits and Systems, vol. 5, No. 6, Dec. 2011, pp. 511-522, DOI: 10.1109/TBCAS.2011.2177661.

Lee et al., "A triple-loop inductive power transmission system for biomedical applications", IEEE Transactions on Biomedical Circuits and Systems, vol. 10, No. 1, 2016, pp. 138-148.

Lee et al., "An integrated power-efficient active rectifier with offset-controlled high speed comparators for inductively powered applications", NIH Public Access Author Manuscript, published in final edited form as: IEEE Trans Circuits and Systems I: Regular Papers, vol. 58, No. 8, 2011, pp. 1749-1760, doi:10.1109/TCSI.2010.2103172.

Li et al., "A 13.56 MHz Wireless Power Transfer System With Reconfigurable Resonant Regulating Rectifier and Wireless Power Control for Implantable Medical Devices", IEEE Journal of Solid-State Circuits, vol. 50, No. 4, Feb. 6, 2015, pp. 978-989, DOI: 10.1109/JSSC.2014.2387832.

Li et al., "Reconfigurable resonant regulating rectifier with primary equalization for extended coupling-and loading-range in bio-implant wireless power transfer", IEEE Transactions on Biomedical Circuits and Systems, vol. 9, No. 6, Dec. 2015, pp. 875-884, doi: 10.1109/TBCAS.2015.2503418.

Lyu et al., "A 100-M/s 2.6-pJ/pulse compact UWB impulse transmitter based on antenna-and-pulse-generator codesign", IEICE Electronics Express, vol. 16, No. 24, Dec. 2, 2019, pp. 1-4, DOI: 10.1587/elex. 16.20190672.

Lyu et al., "A 430-Mhz Wirelessly Powered Implantable Pulse Generator With Intensity/Rate Control and Sub-1 uA Quiescent Current Consumption", IEEE Transactions on Biomedical Circuits and Systems, vol. 13, No. 1, Feb. 2019, pp. 180-190, DOI: 10.1109/TBCAS.2018.2879357.

Lyu et al., "An Energy-Efficient Wirelessly Powered Millimeter-Scale Neurostimulator Implant Based on Systematic Codesign of an Inductive Loop Antenna and a Custom Rectifier", IEEE Transactions on Biomedical Circuits and Systems, vol. 12, No. 5, Oct. 2018, pp. 1131-1143, DOI: 10.1109/TBCAS.2018.2852680.

Lyu et al., "Synchronized Biventricular Heart Pacing in a Closed-chest Porcine Model based on Wirelessly Powered Leadless Pacemakers", Scientific reports, 2020, vol. 10, No. 1, pp. 1-9.

Mirbozorgi et al., "A Single-Chip Full-Duplex High Speed Transceiver for Multi-Site Stimulating and Recording Neural Implants", IEEE Transactions on Biomedical Circuits and Systems, vol. 10, No. 3, Jun. 2016, pp. 643-653, DOI: 10.1109/TBCAS.2015.2466592.

Moh et al., "12.9 A fully integrated 6W wireless power receiver operating at 6.78 MHz with magnetic resonance coupling", IEEE International Solid-State Circuits Conference—(ISSCC) Digest of Technical Papers, Mar. 2015, pp. 1-3, DOI: 10.1109/ISSCC.2015.7063010.

Muller et al., "A Minimally Invasive 64-Channel Wireless uECoG Implant", IEEE Journal of Solid-State Circuits, Jan. 2015, vol. 50, No. 1, pp. 344-359.

O'Driscoll et al., "A mm-sized implantable power receiver with adaptive link compensation", IEEE International Solid-State Circuits Conference-Digest of Technical Papers, Feb. 8-12, 2009, pp. 294-295, DOI: 10.1109/ISSCC.2009.4977424.

Pan et al., "Simultaneous Transmission of Up To 94-mW Self-Regulated Wireless Power and Up To 5-Mb/s Reverse Data Over a

(56) References Cited

OTHER PUBLICATIONS

Single Pair of Coils", IEEE Journal of Solid-State Circuits, vol. 54, No. 4, Feb. 20, 2019, pp. 1003-1016, DOI: 10.1109/JSSC.2018.2888884.

Piech et al., "A wireless millimetre-scale implantable neural stimulator with ultrasonically powered bidirectional communication", Nature Biomedical Engineering, vol. 4, No. 2, Feb. 2020, first published Feb. 19, 2020, pp. 207-222, DOI: https://doi.org/10.1038/s41551-020-0518-9.

Shi et al., "A 10 mm3 Inductive Coupling Radio for Syringe-Implantable Smart Sensor Nodes", IEEE Journal of Solid-State Circuits, Nov. 2016, vol. 51, No. 11, pp. 2570-2583, DOI: 10.1109/JSSC.2016.2606162.

Waters et al., "Powering a ventricular assist device (VAD) with the free-range resonant electrical energy delivery (FREE-D) system", Proceedings of the IEEE, vol. 100, No. 1, Jan. 2012, pp. 138-149, DOI: 10.1109/JPROC.2011.2165309.

Weber et al., "A Miniaturized Single-Transducer Implantable Pressure Sensor With Time-Multiplexed Ultrasonic Data and Power Links", IEEE Journal of Solid-State Circuits, Apr. 2018, vol. 53, No. 4, pp. 1089-1101, DOI: 10.1109/JSSC.2017.2782086.

Xu et al., "A multi-channel neural stimulator with resonance compensated inductive receiver and closed-loop smart power management", 2013 IEEE International Symposium on Circuits and Systems (ISCAS2013), 2013, pp. 638-641, DOI: 10.1109/ISCAS.2013.6571923.

Ye et al., "A Wireless Power and Data Transfer Receiver Achieving 75.4% Effective Power Conversion Efficiency and Supporting 0.1% Modulation Depth for ASK Demodulation", IEEE Journal of Solid-State Circuits, vol. 55, Issue 5, May 2020, first published Oct. 16, 2019, pp. 1386-1400, DOI: 10.1109/JSSC.2019.2943871.

Zargham et al., "A 0.13 µm CMOS integrated wireless power receiver for biomedical applications", Proceedings of the ESSCIRC (ESSIRC), 2013, pp. 137-140.

\* cited by examiner

TABLE II
COMPARISON OF RESONANCE COMPENSATION TECHNIQUES IN POWER-RECEIVING FRONT-ENDS.

| | This work | 2013 ISCAS [28] | 2016 TBioCAS [5] | 2019 JSSC [29] | 2013 ESSCIRC [30] |
|---|---|---|---|---|---|
| Power Frequency | 13.56 MHz | N/A | 13.56 MHz | 13.56 MHz | 160 MHz |
| Capacitor Tuning Range | 6-bit, unit 380 fF | 3-bit, unit 0.51 pF | 10-bit, unit 0.5 pF | 6-bit, unit 2pF | 4-bit, unit 203 fF |
| Detection Target | Swing amplitude | Rectified current | Swing amplitude | Rectified current | Rectified voltage |
| Integrated Resonance Compensation Logic | Yes | Yes | Yes | Yes | Yes |
| Algorithm | Successive approximation | Monotonic sweeping | Monotonic sweeping | Monotonic sweeping | Gradient descent |
| Needed Clock Cycles | 12 | 8 | 512 | 128 | < 128 |
| Silicon Verification | Yes | No | Yes | Yes | Yes |

FIG. 30

TABLE III
COMPARISON OF STATE-OF-THE-ART INDUCTIVE POWER RECEIVERS FOR LOW-POWER IMDs.

| | This work | 2015 JSSC [4] | 2017 JSSC [18] | 2018 JSSC [3] | 2016 TBioCAS [5] |
|---|---|---|---|---|---|
| Power Frequency | 13.56 MHz | 13.56 MHz | 144 MHz | 13.56 MHz | 13.56 MHz |
| Rectifier Type | Passive rectifier | Active rectifier | Active rectifier | Active rectifier | Active rectifier |
| Voltage Regulation Method | Back-telemetry and Tx control | Rectifier modulation; Back-telemetry and Tx control | Rectifier modulation | Rectifier modulation; Back-telemetry and Tx control | LDO; Back-telemetry and Tx control |
| Back-telemetry | UWB | LSK | No | LSK | LSK |
| Input Sensitivity | 2.88 μW | ≈ 3 mW | 20 μW | ≈ 7 mW | 357 μW |
| ΔV$_{OUT}$/V$_{OUT}$ | 0.8% | 3.1% | 187% | 2% | N/A |
| Rx Coil Diameter | 12 mm | 9 mm | 3 mm | 20 mm | 34 mm |
| Load | 10 μA @ 3 V | 16.7 mA @ 3.6 V | 30 μA @ 0.8 V | 2.5 mA @ 2.2 V | 0.6 mA @ 3.3 V |
| Tx-Rx Distance | 2 cm | 0.3 cm | 1 cm | 0.6 cm | 2 cm |
| Power Receiver Efficiency | 46.4% | 92.6% | 50% | N/A | 76.2% |
| End-to-end Efficiency | 16.1% | 50% | 0.4% | 31% | 13.5% |
| Normalized End-to-end Efficiency / Load | 1 | 0.0016 | 0.0312 | 0.0105 | 0.0012 |
| IC Process | 180 nm CMOS | 350 nm CMOS | 180 nm CMOS SOI | 65 nm CMOS | 350 nm CMOS |

FIG. 31

APPARATUS AND METHODS FOR REAL-TIME RESONANCE ADAPTATION FOR POWER RECEIVER

CROSS REFERENCE TO RELATED APPLICATION

This application is a continuation of PCT Patent Application No. PCT/US2021/024888, entitled "Apparatus and Methods for Real-Time Resonance Adaption for Power Receivers" to Lyu et al., filed Mar. 30, 2021, which claims priority to U.S. Provisional Application No. 63/013,797, entitled "Apparatus and Methods for Real-Time Resonance Adaptation for Power Receiver" to Lyu et al., filed Apr. 22, 2020, the disclosures of which are incorporated herein by reference in their entirety.

FIELD OF THE INVENTION

The present invention generally relates real-time resonance adaptation for power receivers and more specifically to an inductive power-receiving system-on-a-chip solution for implantable medical devices (IMDs) and other energy harvesting devices in the power range from few-µW to hundreds-µW.

BACKGROUND

Wireless power transfer has been widely used for medical implants. Real-time and regulated power transfer for implantable medical devices (IMDs) has primarily tackled scenarios where the power consumption of IMDs is in the range from mW to W. Meanwhile, IMDs with less power consumption and the associated invasiveness have become of interest.

SUMMARY OF THE INVENTION

Many embodiments of the invention are directed towards power receiver systems for maximizing power transfer efficiency. One embodiments includes a power receiver system that includes, an inductive coil that receives wireless power from an external transmitter, a capacitor bank that optimizes power transfer to an energy harvesting device, and a power-receiving frontend RF-DC rectifier with a periodically enabled closed feedback loop that adapts settings of the capacitor bank in real-time to adapt to changes on the inductive coil to maximize power transfer efficiency.

In another embodiment, the capacitor bank includes a binary-weighted capacitor bank implemented in parallel with a Dickson-stage passive rectifier.

In a further embodiment, the closed feedback loop mitigates resonance variations due to at least one of different dielectric environments, loading conditions, and fabrication mismatches.

In still another embodiment, the capacitor bank is a 6-bit capacitor bank that is periodically adjusted using a successive-approximation-resonance-tuning process.

In a still further embodiment, the closed feedback loop includes detecting swings corresponding to two consecutive capacitor bank selections and sampling on two hold capacitors respectively.

In yet another embodiment, an impedance of the inductive coil is approximately symmetric against the offset of the resonance capacitor.

In a yet further embodiment, the power receiver includes a transmitter that transmits information to an external controller.

In another additional embodiment, the transmitter is an ultra-wideband impulse radio (IR-UWB) transmitter as a back telemetry for output voltage regulation, where an output voltage from the IR-UWB transmitter is regulated based on back telemetry transmitting the real-time harvested voltage reading.

In a further additional embodiment, operations are heavily duty-cycled to reduce power consumption.

In a further embodiment still, the power receiver system includes a coarse bandgap reference (BGR-course) and a local low-dropout regulator (LDO) that generates a voltage supply for the internal circuitry, and a fine bandgap reference (BGR-fine) that generates a stable voltage reference.

Another embodiment includes a wirelessly powered sensor chip that includes: an inductive coil that receives wireless power from an external transmitter, a capacitor bank that specifies different settings for different external environments surrounding the sensor chip, a power-receiving frontend RF-DC rectifier with a periodically enabled closed feedback loop that adapts settings of the capacitor bank in real-time to adapt to the surrounding environment, and a transmitter that transmits information related to the capacitor settings and voltage readings to an external controller.

In a further embodiment, the capacitor settings are used to determine a type of material in the surrounding environment.

In a further embodiment still, changes to an impedance of the inductive coil result in changes to the capacitor settings and are used to detect near-field changes in the surrounding environment.

In a still further embodiment, changes to a voltage reading without changes to the capacitor settings are used to detect far-field changes in the surrounding environment.

In still a further embodiment, the capacitor bank includes a binary-weighted capacitor bank implemented in parallel with a Dickson-stage passive rectifier In still a further embodiment, the closed feedback loop mitigates resonance variations due to at least one of different dielectric environments, loading conditions, and fabrication mismatches.

In still a further embodiment, the capacitor bank is a 6-bit capacitor bank that is periodically adjusted using a successive-approximation-resonance-tuning process.

In still yet a further embodiment again, the closed feedback loop includes detecting swings corresponding to two consecutive capacitor bank selections and sampling on two hold capacitors respectively.

In yet a further embodiment again, an impedance of the inductive coil is approximately symmetric against the offset of the resonance capacitor.

In still a further embodiment, the transmitter is an ultra-wideband impulse radio (IR-UWB) transmitter as a back telemetry for output voltage regulation, where an output voltage from the IR-UWB transmitter is regulated based on back telemetry transmitting the real-time harvested voltage reading.

BRIEF DESCRIPTION OF THE DRAWINGS

FIG. 30 illustrates a comparison of resonance compensation techniques in power-receiving front-ends in accordance with an embodiment of the invention.

FIG. 31 illustrates a comparison of state-of-the-art inductive power receivers for low-power IMDs in accordance with an embodiment of the invention.

DETAILED DESCRIPTION OF THE DRAWINGS

Figure 1:
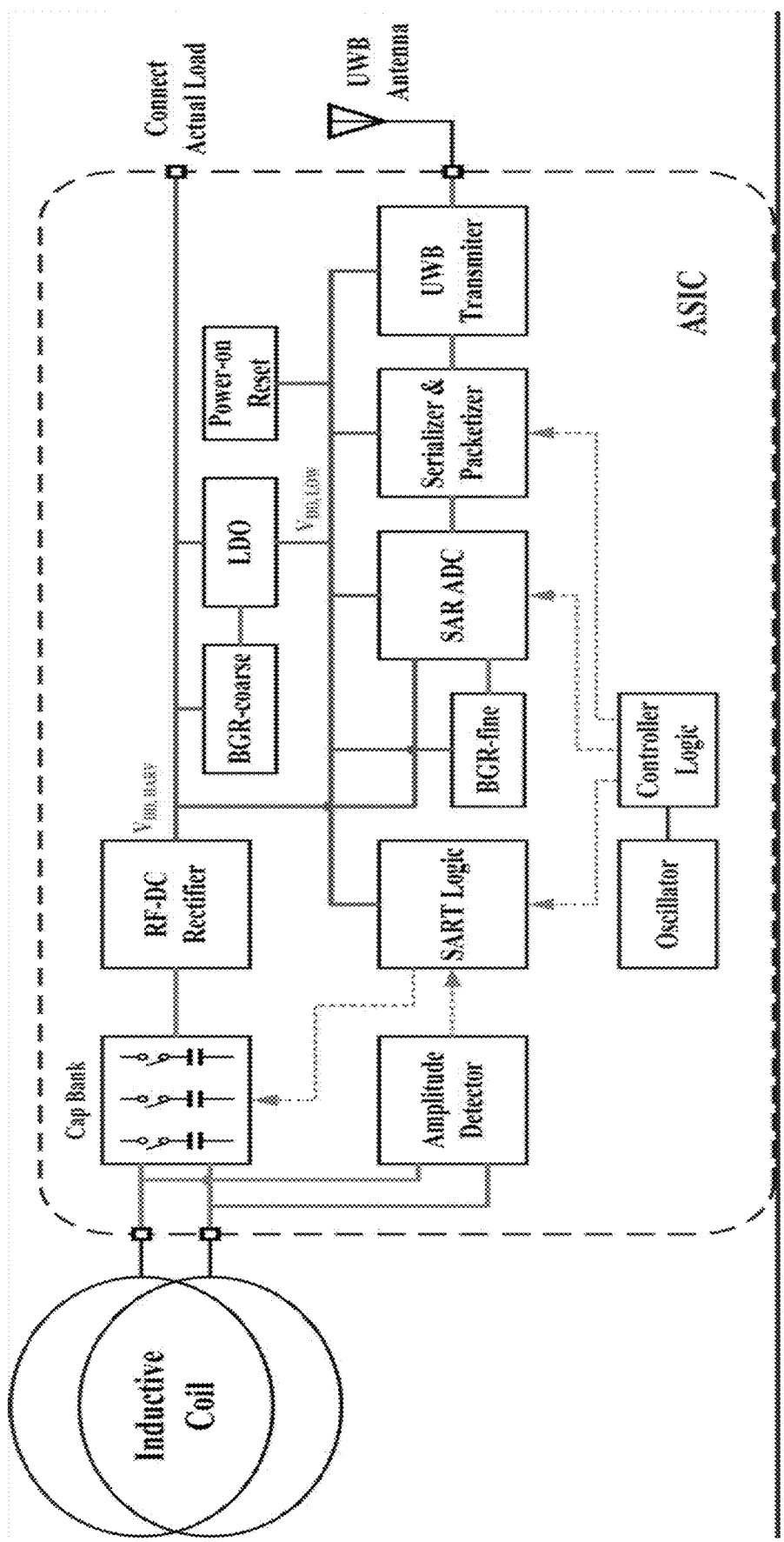
FIG. 1 illustrates a circuit architecture of an inductive power receiver in accordance with an embodiment of the invention.

Turning now to the drawings, systems and methods for inductive power receiver system-on-chip for driving energy harvesting devices, including for example implantable medical devices (IMDs), oil and gas sensors, infrastructure sensors, among numerous other wirelessly powered devices in accordance with embodiments of the invention are illustrated. In particular, implantable medical devices (IMDs) with low power consumption and minimal invasiveness are described. In particular, many embodiments provide an inductive power receiver system-on-a-chip for driving such IMDs. In many embodiments, the power receiver is a 13.56 MHz inductive power receiver system-on-a-chip. In many embodiments, the power receiver can achieve an input sensitivity of −25 dBm (3.41 µW) and efficiency of 45.7% while driving a 10-µA@3-V load. In certain embodiments, the power receiver can include an ultra-wideband impulse radio (IR-UWB) transmitter for back telemetry. Regulated output voltage from 1.7 V to 3.3 V can be achieved from the transmitter via the ultra-wideband impulse radio (IR-UWB) back telemetry carrying the real-time harvested voltage readings. Furthermore, as resonant power transfer improves the transmission efficiency, IMD power receivers may generally suffer from resonance variations due to different dielectric environments and loading conditions. Accordingly, many embodiments provide a real-time resonance adaptation scheme to address this. Furthermore, changes in the resonance variations can be used to sense the surrounding environment (e.g., air, oil, gas) and/or detect changes in the surrounding environment (e.g., bleeding in a patient, changes occurring in an oil/gas pipeline, among numerous other application).

In particular, many embodiments include a capacitor bank that includes switched capacitor units and the particular settings used for the capacitor bank can be adapted and/or optimized using a closed-loop feedback process to maximize the power transfer. In many embodiments, the feedback process adapts in real-time the optimal settings for the capacitor bank to maintain a proper resonance such that $V_{dd,Harv}$ is kept at a maximum in order to maintain good resonance, resolve mismatch, and to deliver higher power to a sensor or other energy harvesting device.

In many embodiments, the logic for tuning the capacitor bank is a periodically enabled successive-approximation-resonance-tuning (SART) logic. In many embodiments, the capacitor bank is a 6-bit capacitor bank with identical switched capacitor units.

In many embodiments, information related to the changed settings of the capacitor bank can be used to sense the surrounding environment and/or detect changes in the environment. In particular, in many embodiments, the values of the capacitor bank and/or voltage readings can be digitized and transmitted to an external controller, and this information can be used to determine various properties of the environment surrounding the sensor chip, and in particular the characteristics of the environment surrounding the inductive coil of the receiving antenna. In many embodiments, the system can measure a rectified voltage and report back the reading using a transmitter, which can be useful for various sensing applications.

As such, the chip can be used as a sensor device for a variety of different applications. In many embodiments, the sensor device can detect the dielectric constant of the surrounding environment, which can be useful for a broad spectrum of different applications (e.g., oil/gas/water infrastructure applications, implantable medical devices, 3D imaging applications, among others). For example, the sensor chip can implanted near a surgical site of a patient and used to measure blood activity or detect bleeding in a patient after surgery.

In particular, different materials in an environment will have different dielectric constants (e.g., Air is 1, Water is 90.2, benzene is 2.3) and based on the particular environment surrounding the chip, including the parasitic capacitance of the inductive coil, the settings of the capacitive bank can be modified using the closed loop process accordingly and these settings can be used to sense the properties of the surrounding environment (e.g., whether the chip is surrounded by water, air, gas, oil, etc., changes in the environment e.g., bleeding in a patient after surgery, bleeding in a vein, near a heart, etc.).

Furthermore, the system can be used as a sensor chip that is able to sense changes in a surrounding environment, both in the near-field and the far-field. The near field and far field are regions of the electromagnetic field (EM) around an object, such as a transmitting antenna, or the result of radiation scattering off an object. Non-radiative 'near-field' behaviors dominate close to the antenna or scattering object, while electromagnetic radiation 'far-field' behaviors dominate at greater distances.

In particular, in many embodiments, the sensor can detect various properties of the surrounding environment including a location (near-field vs. far-field) where the events are occurring. In particular, near-field changes can be sensed as they will change the impendence of the inductive coil and thus can affect both the capacitive bank settings and the harvested voltage. Likewise, far-field changes can be sensed as they may not affect the impedance of the inductive coil and thus will not change the capacitive bank settings, however far-field events may change (e.g., increase or reduce) the harvested voltage and thus the quality of a lossy channel can be monitored. Accordingly, by monitoring these settings over time the system is be able to determine if and where changes in the environment are occurring.

For example, numerous sensor chip can be placed throughout a location and information can be collected across the different sensor chips to detect properties of the surrounding environment. For example, movement of people within a location can be sensed based on changes in the voltage being measured since as people move between a transmitter and a receiver coil, this can reduce the signal strength, and thus the voltage being measured. This information can be gathered from a collection of different sensors located in various positions in a particular location to develop and monitor the 3D location and/or the movement and/or objects within a particular location.

Accordingly, the system in accordance with many embodiments can be used in a variety of different applications, including as a power harvesting system to optimize power transfer to an energy harvesting device and/or a sensor chip that can be used to sense and/or monitor a surrounding environment.

In many embodiments, the system may adapt a capacitor bank to optimize the power transfer based on resonance variations of the inductive coil. In particular, the circuit may converge to the optimal resonance capacitor within a number of clock cycles (e.g., 12 clock cycles) at a minimal power dissipation cost. In many embodiments, the system can be fabricated in 180-nm CMOS process, and the system features an overall current dissipation of 900 nA. In many embodiments, the system can be immune to resonance capacitor offsets with a precise compensation accuracy. For example, at a 2-cm distance, the end-to-end efficiency may equal 14.8% regardless of an artificially induced 10-pF offset while driving the 30-μW load. Such resonance adaptability improves the power link efficiency by orders of magnitude for realistic IMDs depending on the specific load.

As noted, wireless power transfer has been widely used for medical implants. Prior art implementations in real-time and regulated power transfer for implantable medical devices (IMDs) has primarily addressed scenarios where the power consumption of IMDs is in the range from mW to W. Meanwhile, IMDs with less power consumption and the associated invasiveness have become one of the latest paradigms. As the power consumption of IMDs may be reduced to tens-μW or less, the power link can be substantially elongated with a moderate Tx power, and thus can open be used for many therapeutic applications. These IMDs can also form distributed sensory and actuation systems in place of conventional centralized counterparts. The cardiac sensing and pacing network based on wirelessly powered microdevices directly implanted in the heart is an example of such system. In particular, the continuous movement may require frequent and periodic adaptation of the energy-harvesting front-end.

Sophisticated designs of wireless power transfer systems in the power ratings from few-μW to hundreds-μW have not been insensitively discussed in the prior art. These systems should prioritize sensitivity and stress less on the power transfer efficiency which tends to be higher for heavier loads. Therefore, in terms of the rectification topology, active rectifiers consisting of power-hungry high-speed comparators may be replaced with optimally designed passive rectifiers.

As noted above, a challenge for energy-harvesting IMDs is the vulnerability to resonance variations, which could be induced from, for example, fabrication mismatches, different implantation sites, movement, buildup of scar tissue, and varying load conditions, among many other reasons. The actuation device, in particular, can pose a different equivalent input capacitance of the rectifier depending on the stimulation strength and on/off status. An approach has been to purposefully decrease the quality factor in a trade-off for a wider bandwidth, which, of course, sacrifices the optimal efficiency. Accordingly, many embodiments of the system provide for an active compensation method, where a capacitor bank is adaptively tuned to compensate for resonance variations. Accordingly many embodiments provide for an implementation of such circuit that can converge to the optimal solution fast and cause negligible power consumption overhead that would otherwise hamper the sensitivity of the system.

Another challenge may be the output voltage regulation. A way that has been used to regulate the harvested power can be a cascaded two-step approach, e.g., RF-DC rectification and DC regulation, with the corresponding two-step losses. To combine the two stages, the resonant regulating rectification method has been adopted, where the operation of the rectifier is duty-cycled to stabilize the output voltage. However, the high-speed comparators in the active rectifiers pose a challenge for low-power IMDs. The method is also associated with excessive output voltage fluctuations.

Accordingly, many embodiments provide for an inductive power (e.g., 13.56 MHz inductive power) receiver system-on-a-chip for IMDs in the power range from few-$\mu$W to hundreds-$\mu$W. Many embodiments of the inductive power receiver are able to achieve an input power sensitivity of a few $\mu$W (e.g., 2.88 $\mu$W) and regulate the output voltage within a certain range (e.g., 1.7 V to 3.3 V with over 40 dB regulation). In many embodiments, an ultra-wideband impulse radio (IR-UWB) back-telemetry can be employed to transmit the digitized output voltage. Many embodiments of the power receiver are able to address resonance variations, which has been an issue for power-receiving IMDs, by using a successive-approximation-resonance-tuning (SART) technique, which offers a compensation dynamic range (e.g., 6-bit compensation dynamic range) and may cause negligible power consumption overhead. For example, targeting a 30-$\mu$W load at the link distance of 2 cm, the system in accordance with an embodiment of the invention is able to achieve an end-to-end efficiency of 16.1% regardless of an artificially induced 10-pF resonance capacitor offset. The resonance adaptation technique in accordance with many embodiments improves the power transfer efficiency by orders of magnitude for realistic IMDs.

Described in detail are the overall architecture of the power receivers, implementations of the adaptive resonance process including SART, optimizations of rectifiers, magnetic links, implementations of ADC and IR-UWB back-telemetry for voltage regulation from the transmitter, and measurement results and comparisons in accordance with many embodiments of the invention.

System Overview

Figure 2:
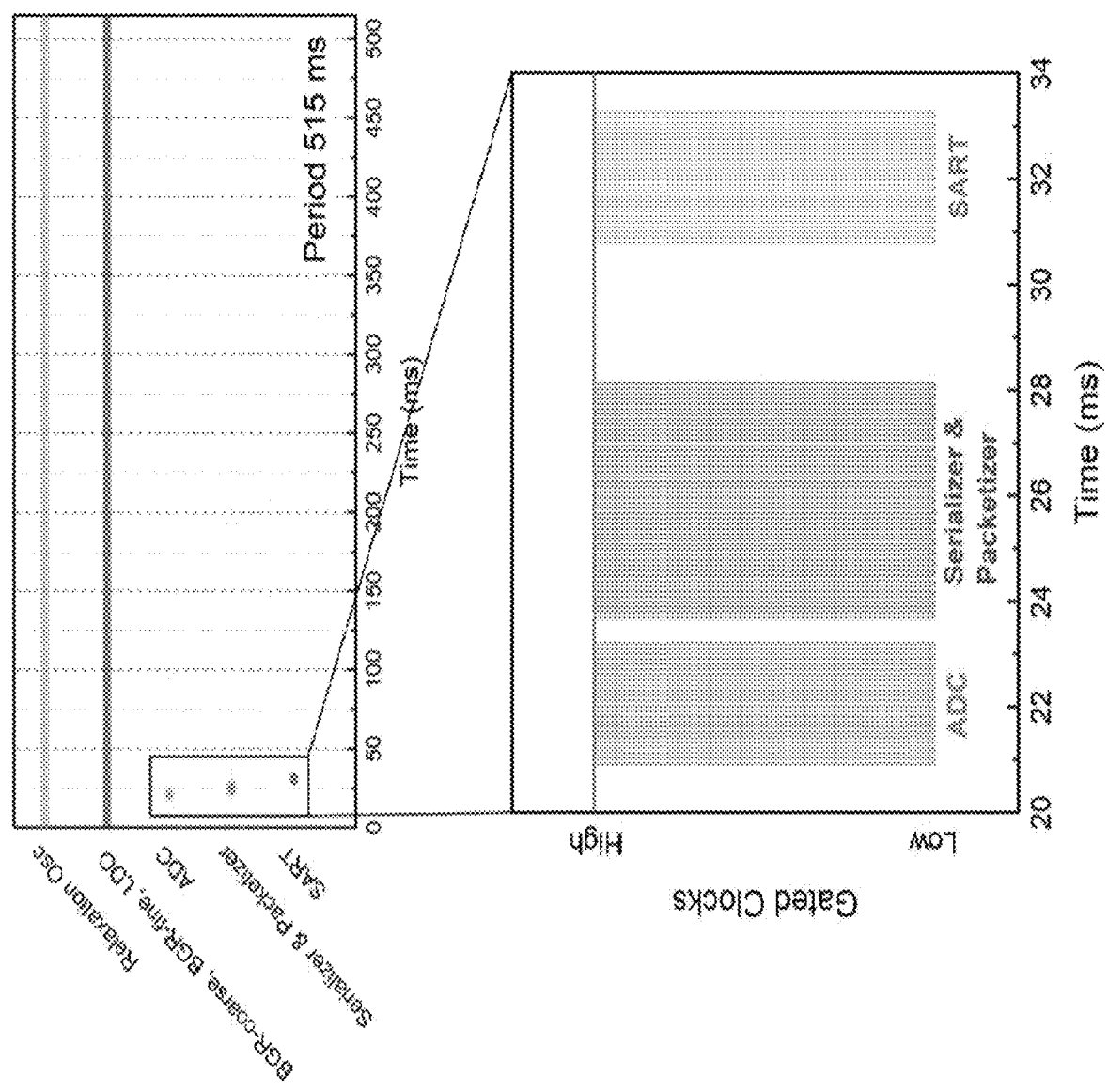
FIG. 2 illustrates a system timing schedule for duty-cycling in accordance with an embodiment of the invention.

An overall block diagram of an inductive power receiver in accordance with an embodiment of the invention is illustrated in FIG. 1. The circuit illustrated in FIG. 1 can include, among various other circuitry, an inductive coil, a capacitor bank, a rectifier, a transmitter, and a closed feedback loop for optimizing settings of the capacitor bank based on changes in the resonance frequency of the inductive coil. In many embodiments, the IC circuit can include an RF-DC rectifier with SART, an SAR ADC (e.g., a 7-bit SAR ADC) for digitizing a harvested voltage, $V_{DD,HARV}$, and an IR-UWB transmitter as the back-telemetry. In many embodiments, their operations can be heavily duty-cycled to reduce the power consumption as shown in the schedule map in FIG. 2 in accordance with an embodiment of the invention. The clock signal in accordance with many embodiments can be generated by a relaxation oscillator (e.g., a relaxation oscillator running at approximately 5 kHz). Each SART execution may last less than a certain percentage of the system cycle (e.g., 0.5% of the system cycle), and therefore, may not hamper the power-receiving efficiency. The system cycle, including SART, voltage digitization, and back-telemetry operations can be executed at a particular Hz (e.g., about 2 Hz) to address the ever-changing dielectric environments and loading conditions.

In many embodiments, a coarse bandgap reference (BGR-course) and a local low-dropout regulator (LDO) implemented in 3.3-V process can generate the voltage supply for the internal circuitry at approximately 1.6 V. Another fine bandgap reference (BGR-fine) can create a stable voltage reference with a power-supply-rejection-ratio (PSRR) over 60 dB. In many embodiments, the ADC can be designed with seven effective bits to provide 42 dB regulation of the output voltage. An IR-UWB transmitter can be implemented as the back-telemetry due to its low power consumption and potential sharing with other bioelectric sensory functions. In many embodiments, an n-bit header (e.g., a 4-bit header) and an n-bit ADC (e.g., 7-bit ADC output) forming e.g., 11 bits can be serially streamed to the transmitter. Although FIG. 1 illustrates a particular circuit architecture for an inductive power receiver, any of a variety of circuit architectures for inductive power receivers and/or sensors can be utilized as appropriate to the requirements of specific applications in accordance with embodiments of the invention.

Power-Receiving Front-End with Successive Approximation Resonance Tuning

A parallel capacitor, $C_P$, may be typically needed to tune the resonant frequency of the receiving coil to boost the voltage swing and improve the power transmission efficiency. Research has focused on active compensation for any resonance variations by tuning the resonance capacitor. Certain prior art designs may employ thermometer-coded capacitors based on PMOS varactors to realize a 3-bit dynamic range, and implement binary-weighted capacitor banks at the rectifier input. On-chip optimization logics have been implemented as the hill-climbing algorithm, in which each step of operation only adapts to an adjacent code. Therefore, the convergence time exponentially grows with the dynamic range. Certain prior art implementations propose a gradient descent algorithm with concerns on the logic complexity and the associated power consumption. Also, the work monitors the rectified output voltage requiring excessive time before stabilization. It is noteworthy that for most IMDs, resonance compensation is not only needed as a one-time calibration, as the dielectric environment and loading condition may change over time.

To address these challenges, many embodiments the inductive power receiver provide for an algorithm (e.g., SART logic circuitry) which can accurately and timely compensate for any resonance capacitor offsets. SART can be periodically executed to address the ever-changing resonance variations while the rectifier can continuously salvage the inductive power. These techniques in accordance with many embodiments can be applied to a variety of energy-harvesting IMDs.

Architecture and Compensation Logic

Figure 3:
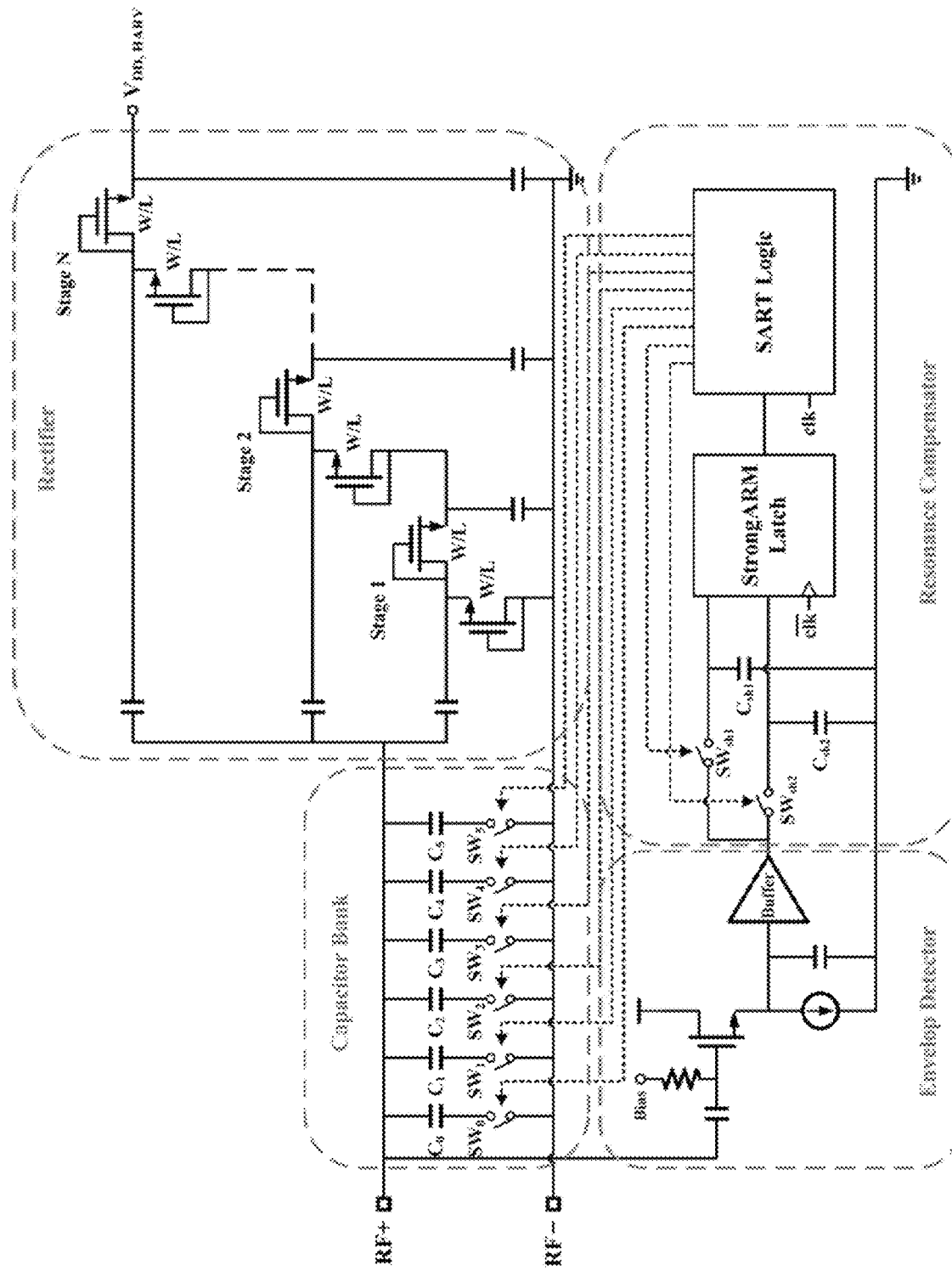
FIG. 3 illustrates a circuit schematic of a power-receiving front-end with SART in accordance with an embodiment of the invention.

A circuit schematic of a power-receiving front-end with SART in accordance with an embodiment of the invention is illustrated in FIG. 3. In many embodiments, a capacitor bank can be implemented with a rectifier. In certain embodiments, a 6-bit binary-weighted capacitor bank can be implemented in parallel with a Dickson-stage passive rectifier. Each capacitor bank selection can lead to a variation in the RF signal amplitude. In many embodiments, the swings corresponding to two consecutive capacitor bank selections can be detected and sampled on two hold capacitors, respectively. The comparison between the two can be made by a zero-static-power StrongARM latch comparator as the input to the SART logic. Although FIG. 3 illustrates a particular circuit schematic of a power-receiving front-end with SART, any of a variety of circuit designs may be specified as appropriate to the requirements of specific applications in accordance with embodiments of the invention.

Figure 4:
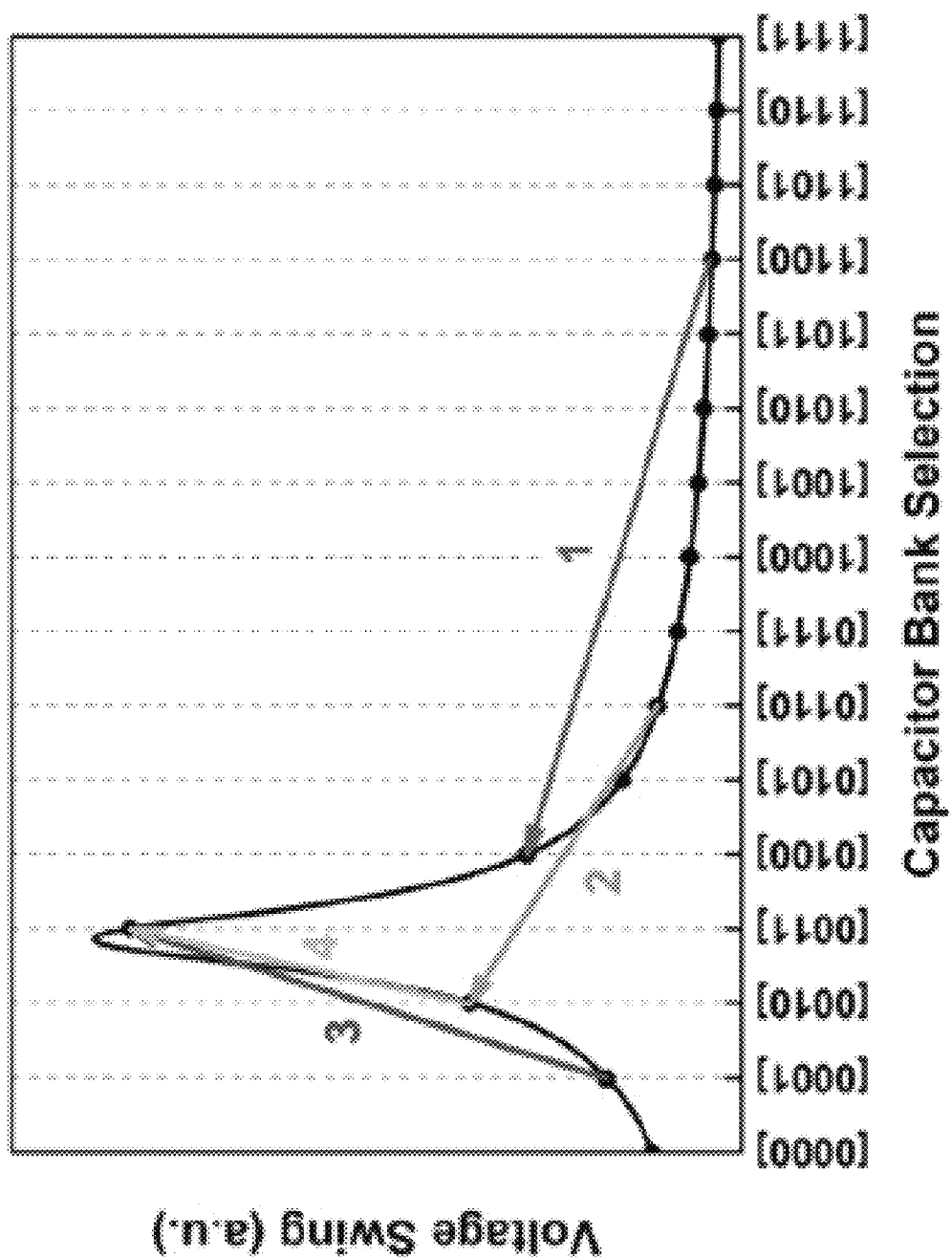
FIG. 4 illustrates a successive approximation process in a 4-bit scenario in accordance with an embodiment of the invention.

In many embodiments, the impedance of a coil can be approximately symmetric against the offset of the resonance capacitor. And the higher impedance may lead to a larger voltage swing. Therefore, many embodiments of the power receiver provide for a resonance compensation algorithm that adapts the capacitor bank to achieve the maximum voltage swing. A SART process in accordance with an embodiment of the invention is illustratively in FIG. 4 in a 4-bit scenario. The process can start from comparing ¼ and ¾ of the full-scale dynamic range, e.g., '0100' and '1100', and the result can be updated as the MSB. Then, the process can compare ¼ and ¾ of the rest of the range, e.g., 'MSB,010' and 'MSB,110', with the result updated as the second significant bit, and so forth.

Figure 5:
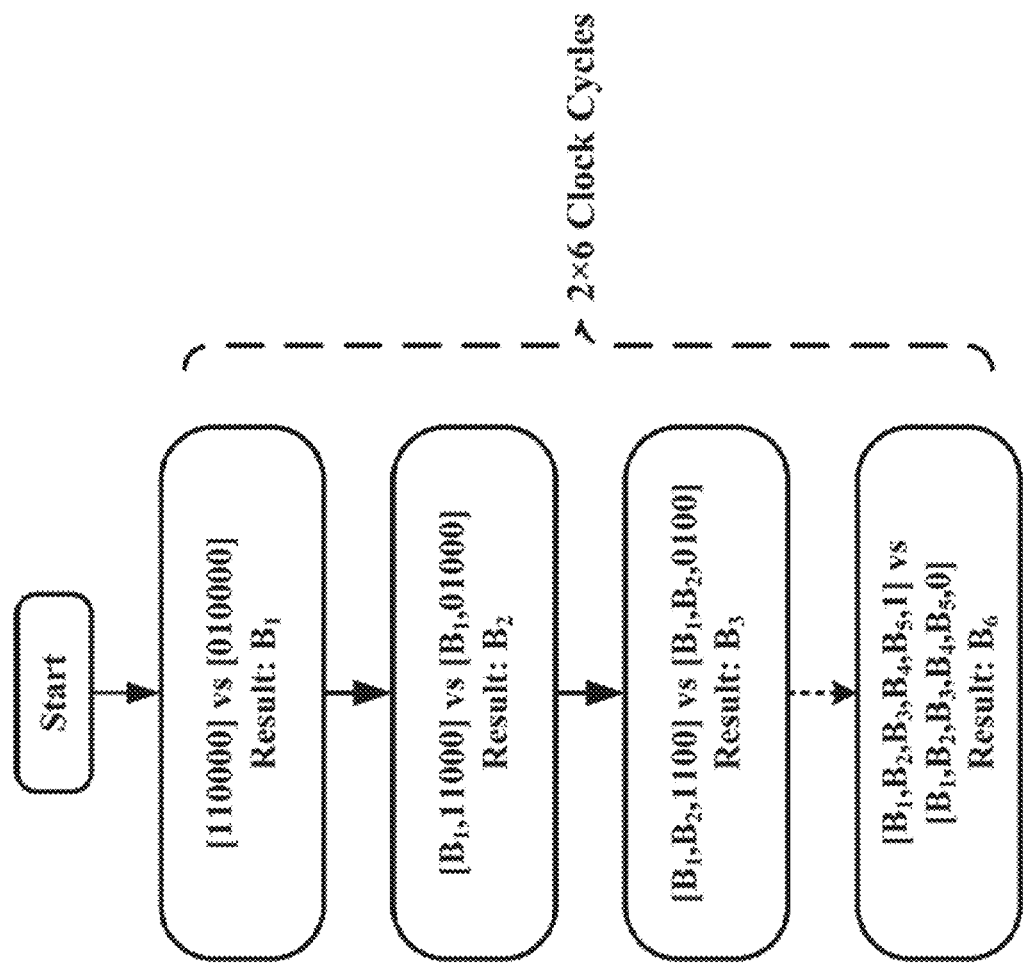
FIG. 5 illustrates a logic flow process for the adaption of a 6-bit SART in accordance with an embodiment of the invention.

For an N-bit dynamic range, the process may require N such comparisons, or 2N clock cycles, to achieve the optimal selection code. The convergence time of SART may be proportional to the dynamic range, while the prior art exhibits an exponential relationship. A complete logic-flow chart for adapting a 6-bit capacitor bank in accordance with an embodiment of the invention is illustrated in FIG. 5. Although FIG. 5 illustrates a particular process for a 6-bit SART, any of a variety of processes may be utilized as appropriate to the requirements of specific applications in accordance with embodiments of the invention.

Rectifier

Figure 6:
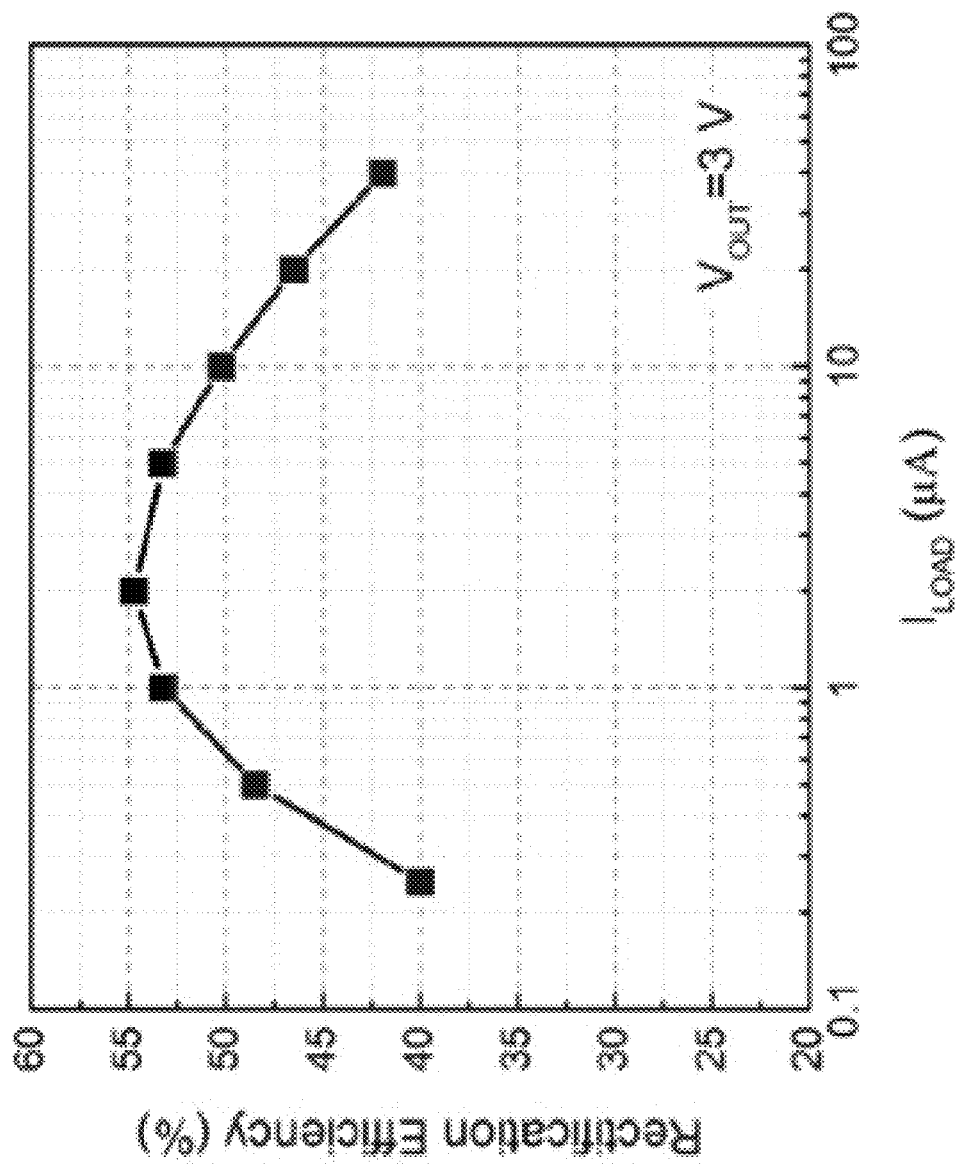
FIG. 6 illustrates rectifier efficiencies for different $I_{LOAD}$ at $V_{OUT}$ of 3 V in accordance with an embodiment of the invention.
Figure 7:
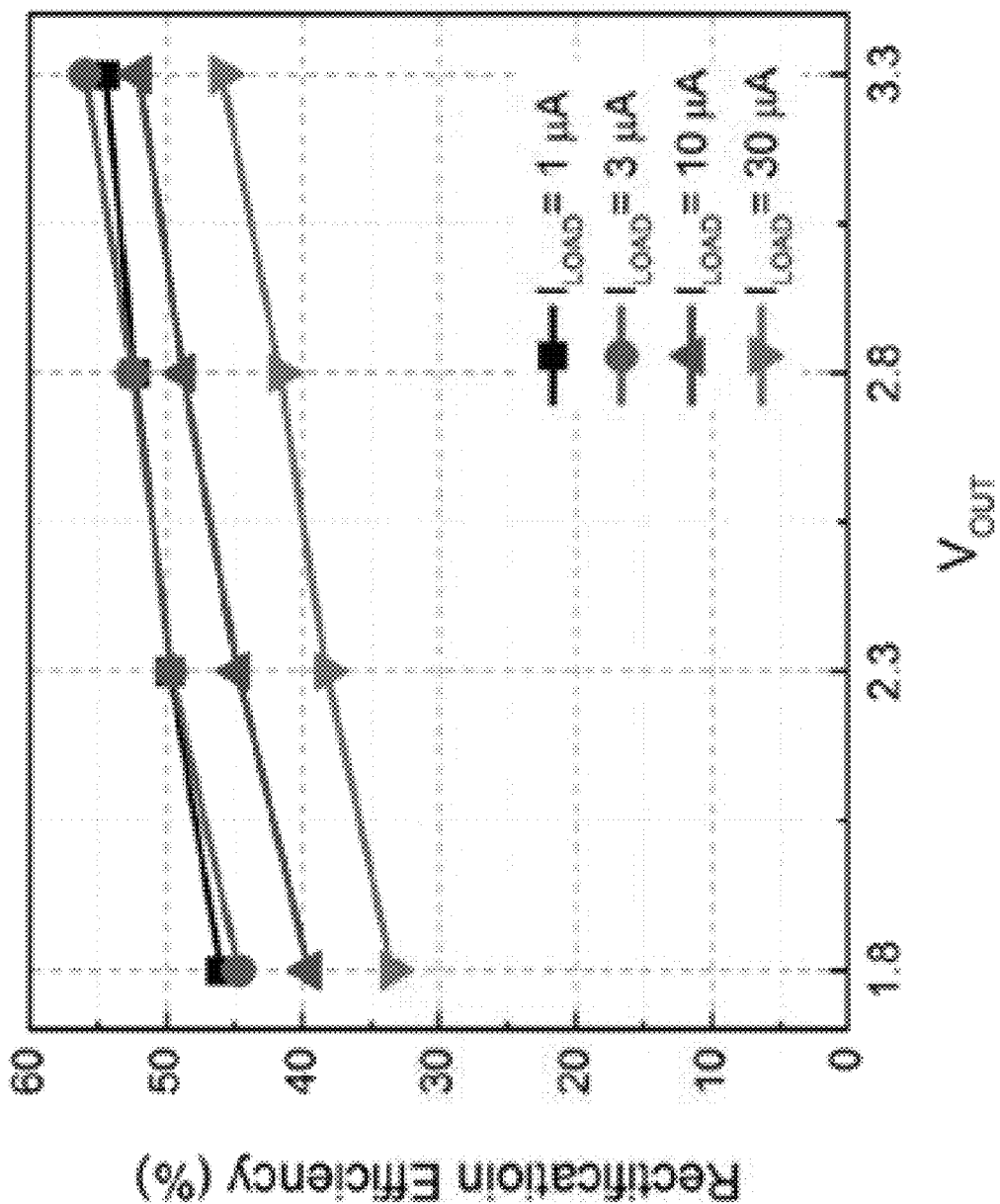
FIG. 7 illustrates rectifier efficiencies at different $V_{OUT}$ for $I_{LOAD}$ of 1 µA, 3 µA, 10 µA, and 30 µA, respectively in accordance with an embodiment of the invention.

In many embodiments, a passive rectifier can include N stages (N=5) and employ native transistors to boost the rectification efficiency. The load current, $I_{LOAD}$, on the order of few-μA can be a design target, which represents the dissipation of typical IMDs. In an embodiment, the width of each transistor can be sized to be 5 μm while the gate length is kept at a minimal value of 0.5 μm. The simulated rectification efficiency versus $I_{LOAD}$ is shown in FIG. 6 in accordance with an embodiment of the invention. It may exceed 50% for $I_{LOAD}$ from 0.6 μA to 10 μA. The optimal gate-sizing for other load ratings can be achieved by proportionally scaling up or down the transistors' width, while in the high-power regime, active rectifiers may result in better efficiencies. The rectification efficiency against the output voltage, $V_{OUT}$, is illustrated in FIG. 7 in accordance with an embodiment of the invention demonstrating stable performances for the targeted loads.

Switched Capacitor Bank

Figure 8B:
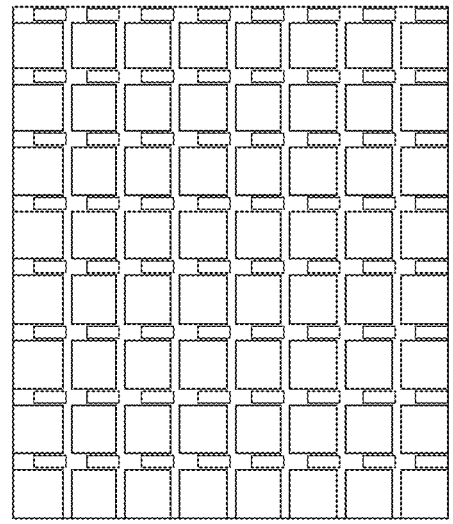
FIG. 8 illustrates (a) circuit schematic of each switched capacitor unit and (b) layout of a 6-bit switched capacitor bank array in accordance with an embodiment of the invention.
Figure 8A:
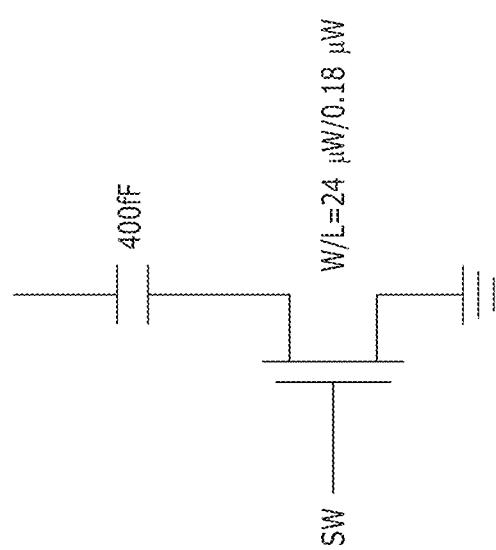

Switched capacitors in binary-weighted values for resonance compensation front-ends could easily suffer from nonlinearity issues due to fabrication mismatches. Accordingly, many embodiments of the power receiver implement a capacitor bank as identical unit cells with metal-insulator-metal capacitor and NMOS switch. In many embodiments a capacitor bank can be implemented as 63 identical unit cells each having a 400-fF metal-insulator-metal capacitor and an NMOS switch with W/L=24 μm/0.18 μm as illustrated in the FIG. 8 item (a) in accordance with an embodiment of the invention, which can contribute to a sufficiently high quality-factor of approximately 1000 or dissipation factor of ¹⁄₁₀₀₀ according to circuit simulation (note that it is only the quality factor or dissipation factor of a switched capacitor unit, not the Rx tank). Due to the parasitic capacitance of the switch, the unit cell may exhibit an equivalent capacitance of approximately 20 fF in the off state. Therefore, the tuning resolution may be 380 fF and the overall range equals 24 pF. A layout of a capacitor bank is illustrated in FIG. 8(b) which illustrates a layout of a 6-bit switched capacitor bank array in accordance with an embodiment of the invention. Although FIG. 8 illustrates a particular circuit schematic of each switched capacitor unit and a layout of a 6-bit switched capacitor bank array, any of a variety of circuit designs may be specified as appropriate to the requirements of specific applications in accordance with embodiments of the invention.

Magnetic Coupling Link

Figure 9:
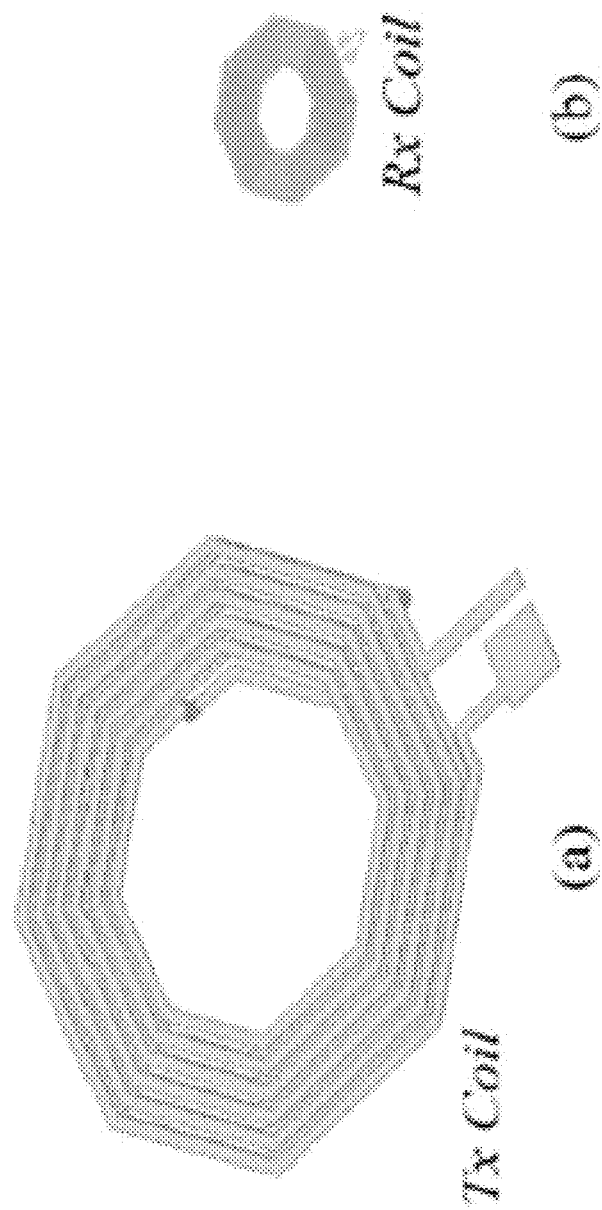
FIG. 9 illustrates Tx and Rx coils in accordance with an embodiment of the invention.

Designs of Tx and Rx coils in accordance with an embodiment of the invention are illustrated in FIG. 9 and Table I in FIG. 9 demonstrates certain key parameters. An Rx coil can be designed with a small diameter (e.g., of 12 mm) to fit miniaturized IMDs. The inductances of the Tx and Rx coils can be simulated to be 5.76 μH and 6.36 μH, respectively. A 21.7-pF parallel capacitor, $C_P$, may be required to make the Rx coil resonate at 13.56 MHz, and the Tx coil may employ an additional L-matching section to match the 50-Ω power source.

Figure 10:
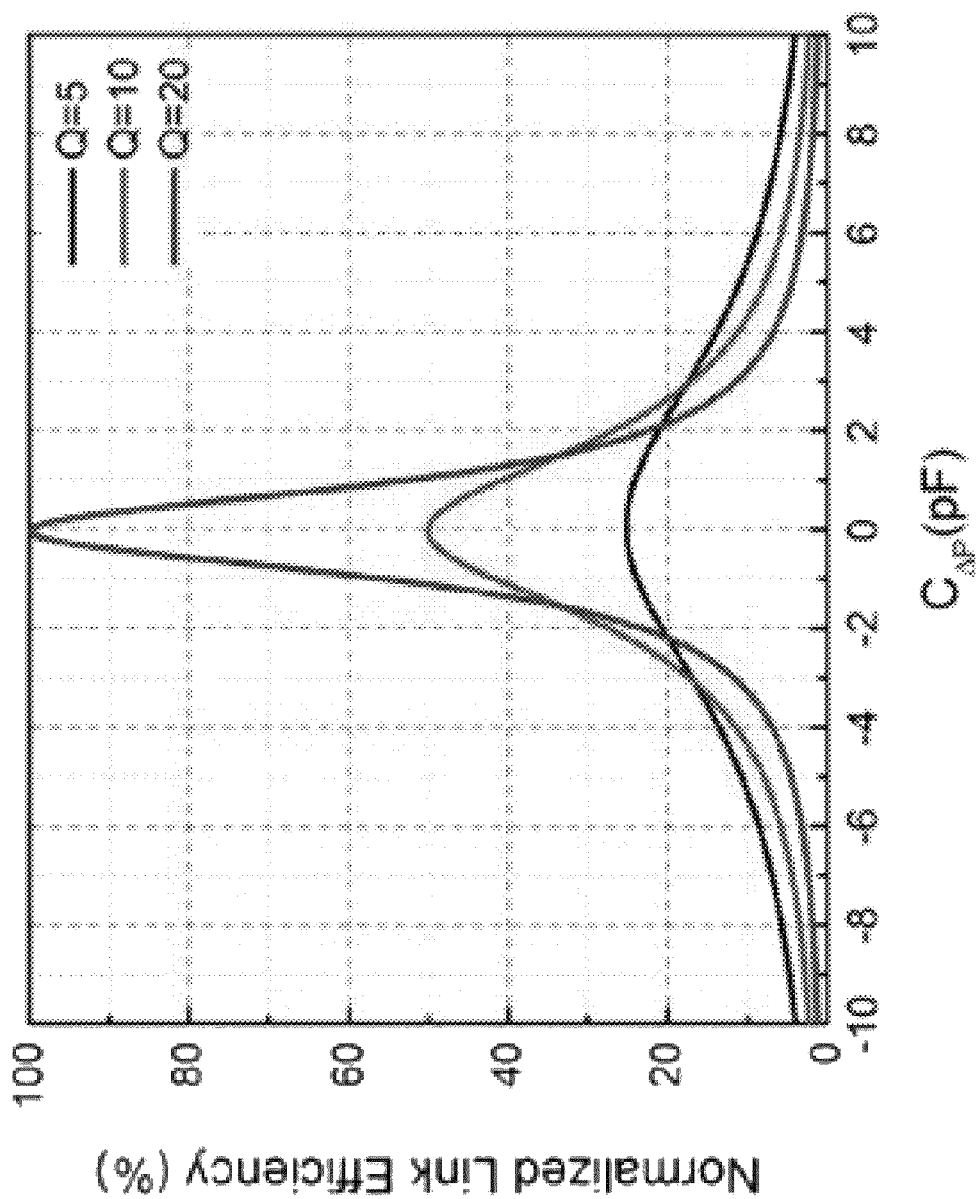
FIG. 10. illustrates normalized link efficiency against the resonance capacitor offset in the Rx coil in accordance with an embodiment of the invention.

The offset of $C_P$, $C_{ΔP}$, may affect the voltage swing and, therefore, the power transfer efficiency. $C_{ΔP}$ up to 10 pF is considered, which mimics realistic situations when the Rx coil is placed in different dielectric media, for example, in water as a contrast to in the air. The power transfer efficiency for different $C_{ΔP}$ can be normalized as shown in FIG. 10 in accordance with an embodiment of the invention. As expected, systems with higher quality factors can be more vulnerable to the offset. Although FIG. 9 illustrates a particular design of a Tx and Rx coil with certain key parameters, any of a variety of Tx and Rx designs may be specified as appropriate to the requirements of specific applications in accordance with embodiments of the invention.

Voltage Regulation and UWB Telemetry

Conventional wireless power receivers typically employ separate LDOs to regulate rectified voltages. The two-step conversion incurs additional inefficiency. Also, two large decoupling capacitors are typically required before and after the regulation to reduce the ripple of the harvested voltage and to stabilize the regulation feedback, respectively. The resonant regulating rectification scheme is associated with timing-induced losses of the comparators. To address the challenge, either power-hungry high-speed comparators can be used or the system's complexity can be significantly increased with the adoption of latency-compensation schemes.

Accordingly, many embodiments of the power receiver regulate the harvested voltage from the transmitter via an on-chip voltage digitization and back-telemetry. In many embodiments, a 7-bit ADC provides about 42 dB regulation ratio. An IR-UWB transmitter with negligible power consumption can be implemented for potential sharing with other sensory functions as well.

SAR ADC

Figure 11:
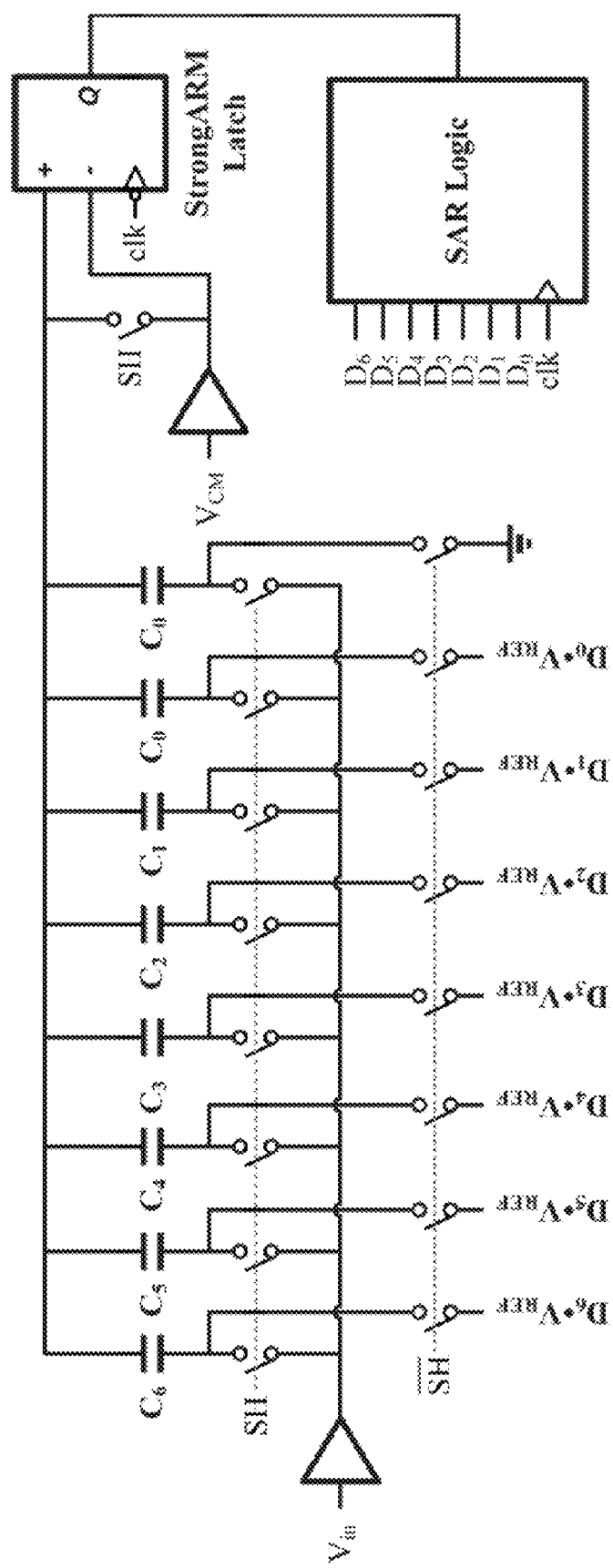
FIG. 11 illustrates a circuit schematic of a bottom-sampling SAR ADC in accordance with an embodiment of the invention.

In many embodiments, a bottom-plate sampling SAR ADC can be implemented. FIG. 11 illustrates a bottom-plate sampling SAR ADC with a 7-bit dynamic range in accordance with an embodiment of the invention. In many embodiments, all sample-and-hold buffers can be power-gated only for the operation duration as shown in FIG. 3 to minimize power consumption. The 7-bit ADC output can be serialized and packetized with a '0101' header for back-telemetry transmission. Although FIG. 11 illustrates a particular circuit schematic of a bottom-plating sampling SAR ADC, any of a variety of circuit schematics may be specified as appropriate to the requirements of specific applications in accordance with embodiments of the invention.

UWB Transmitter

Figure 12:
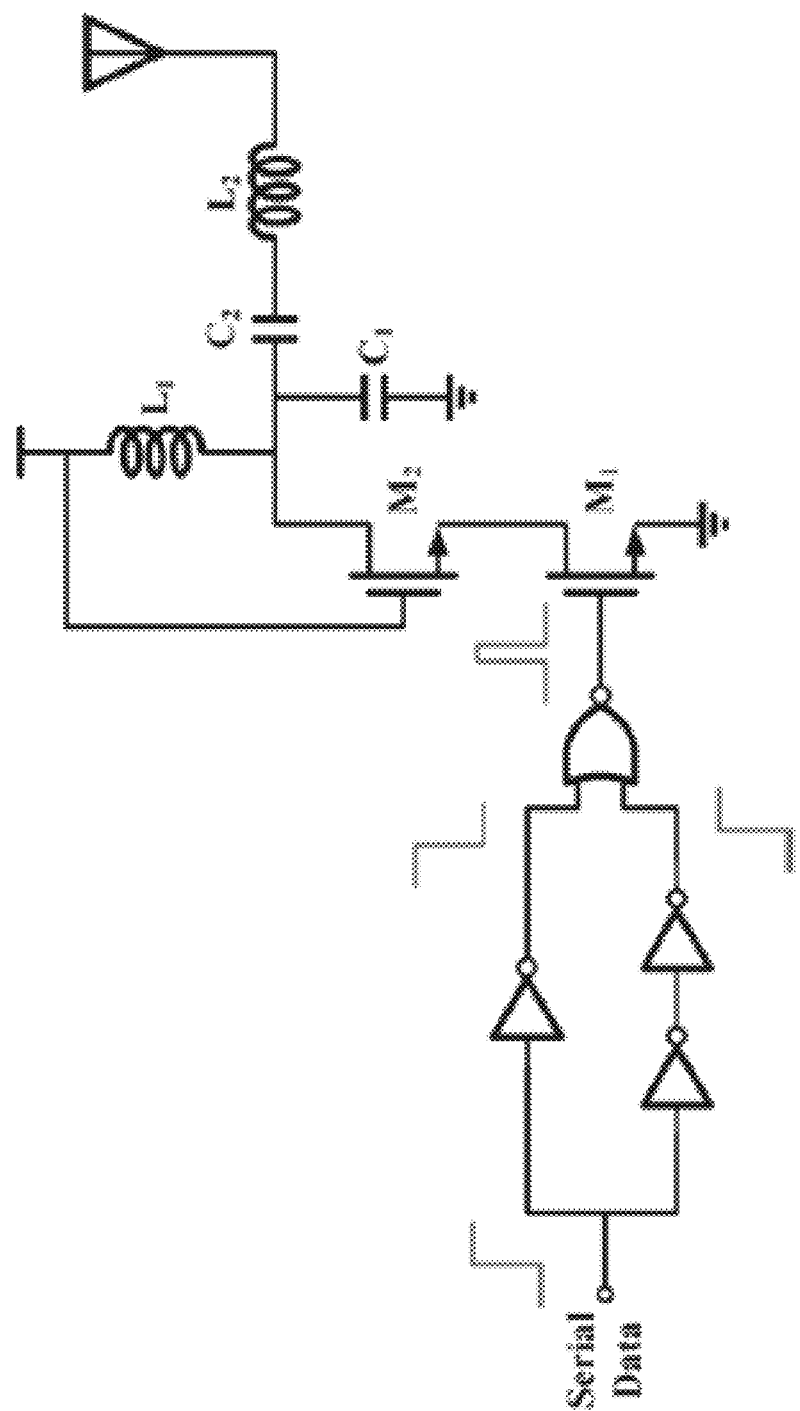
FIG. 12 illustrates a circuit schematic of an IR-UWB transmitter in accordance with an embodiment of the invention.

IR-UWB has been widely used in IMDs due to its low power consumption and miniaturized antenna form factors. Accordingly, many embodiments of the power receiver employ a filtered edge-combining technique for generating FCC-compliant UWB impulses. A mono-pulse can be initially generated from a delay cell and subsequently passed through an on-chip passive filter as shown in the schematic in FIG. 12 in accordance with an embodiment of the invention.

Figure 13:
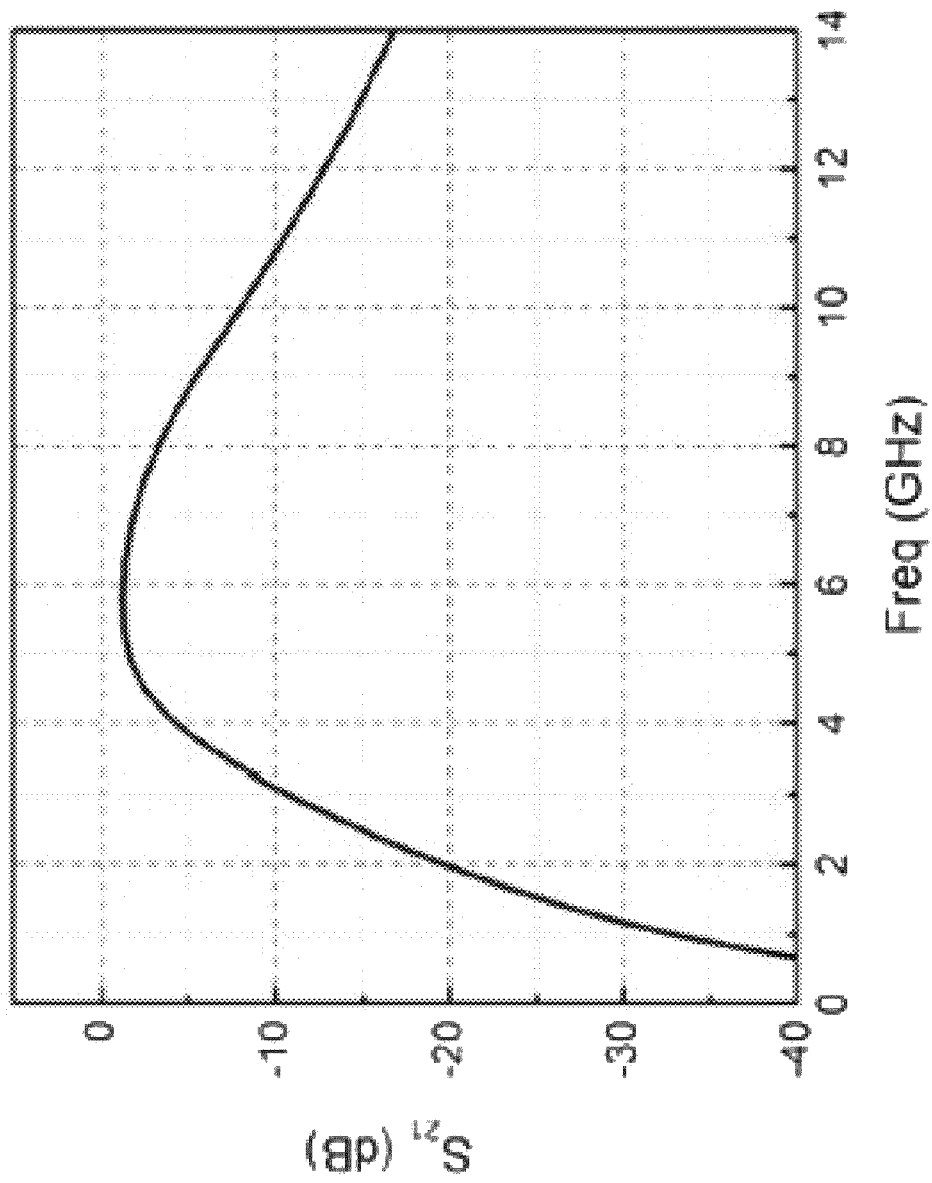
FIG. 13 illustrates $S_{21}$ of an on-chip UWB filter in accordance with an embodiment of the invention.
Figure 14:
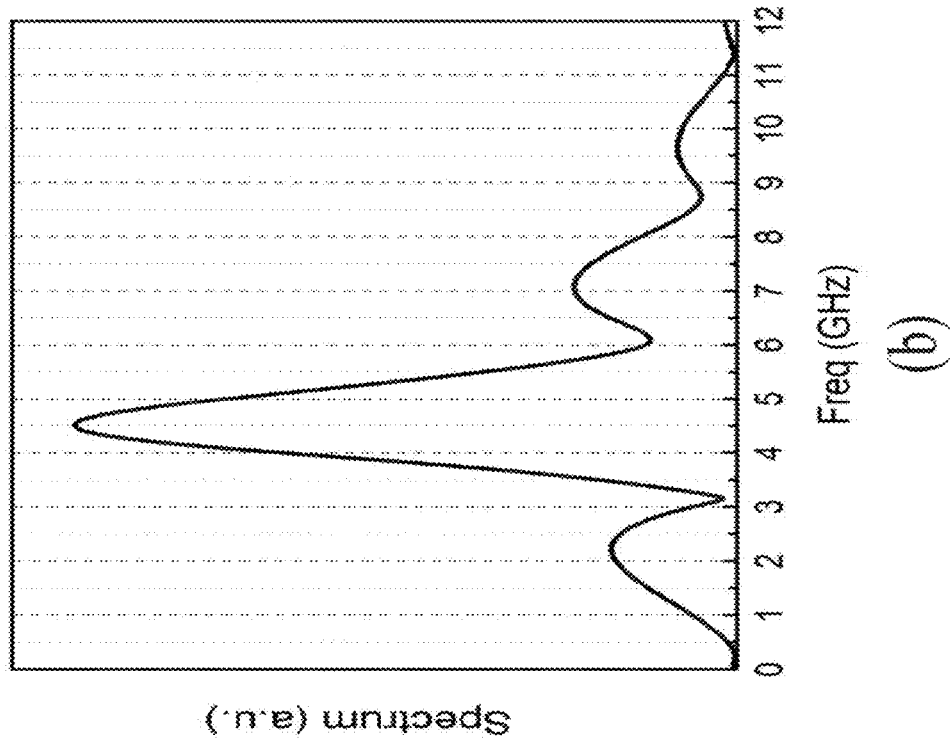
FIG. 14 illustrates (a) transient waveform and (b) frequency spectrum of a UWB impulse in accordance with an embodiment of the invention.
Figure 14:
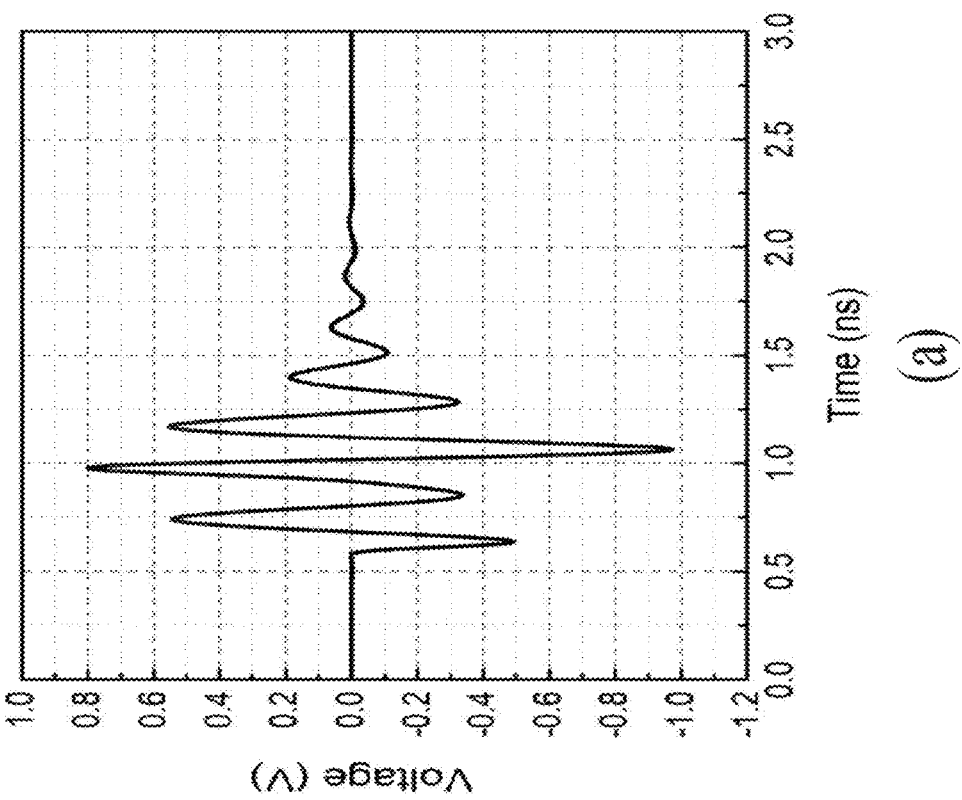

$M_1$ may operate in class-C and the upper cascode transistor, $M_2$, can be implemented to avoid voltage overshooting. In many embodiments, the values of the filter components, $C_1$, $C_2$, $L_1$, and $L_2$ equals 981 fF, 444 fF, 614 µH, and 1.69 nH, respectively. The estimated drain capacitance of $M_2$ equals 221 fF and can be absorbed to $C_1$ to determine the filtering characteristics as shown in FIG. 13. The transient waveform of each emitted impulse on a 50-Ω load and the corresponding frequency spectrum are shown in FIGS. 14(a) and (b), respectively in accordance with an embodiment of the invention. In particular, FIG. 14(a) illustrates a transient waveform and FIG. 14(b) illustrates a frequency spectrum of the UWB impulse. In many embodiments, the system may only require transmitting about twenty impulses per second, which easily complies with the FCC emission mask.

In many embodiments, since the transmitter is triggered by the positive edge, the input symbols can be first converted to return-to-zero formats.

Each logical '1' and logical '0' can be converted to '10' and '00', respectively. Hence, the symbol rate of the transmitter can be half of the clock frequency. Each impulse can be simulated to consume about 65.6 pJ (DC energy) and the emitted energy is about 2.7 pJ. Twenty emissions per second correspond to the power dissipation of 1.3 nW.

Measurements

Figure 15:
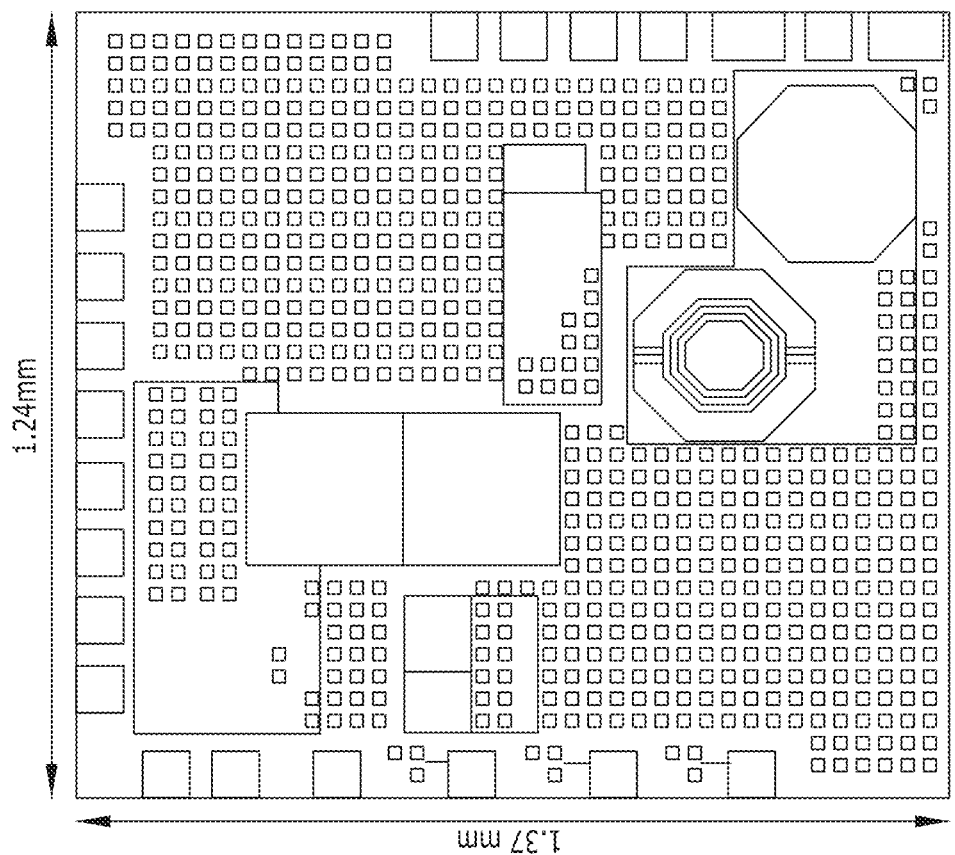
FIG. 15 illustrates a microscopic picture of a power receiver IC in accordance with an embodiment of the invention.
Figure 16:
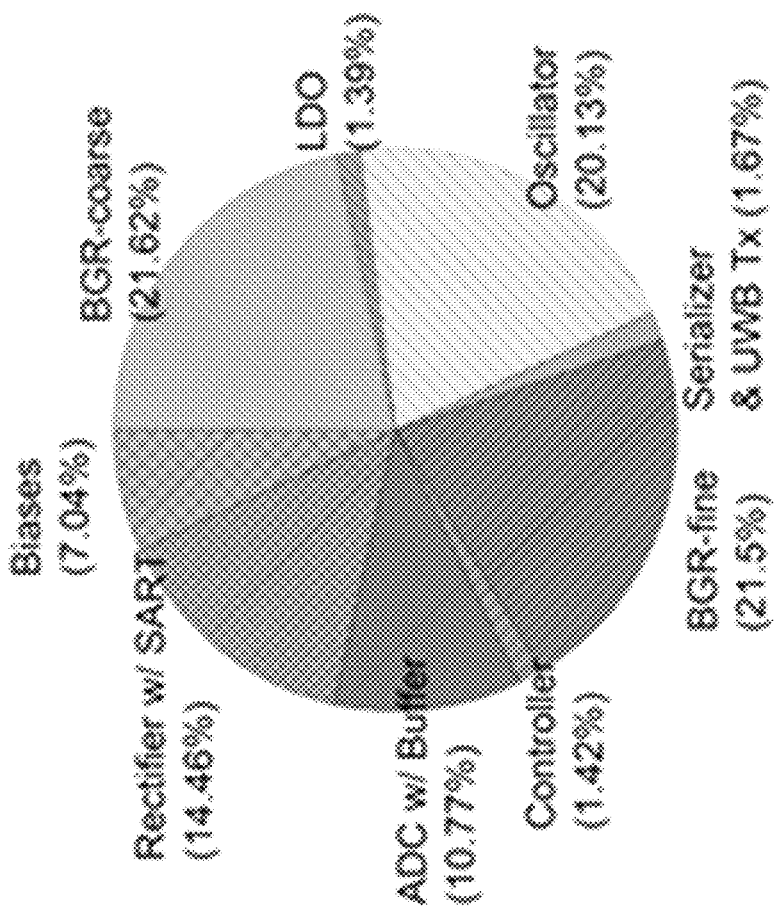
FIG. 16 illustrates a power breakdown in accordance with an embodiment of the invention.

An IC in accordance with many embodiments can be fabricated in 180-nm CMOS process with a microphotograph as illustrated in FIG. 15. The overall size of the IC can be about 1.7 mm2. Its current dissipation is measured to be 750 nA. In many embodiments, the IC can operate at a minimal $V_{DD,HARV}$ of 1.7 V, which may require an input power of 2.88 µW or −25.4 dBm that defines the sensitivity of the system. A power breakdown chart is illustrated in FIG. 16 in accordance with an embodiment of the invention.

Figure 17:
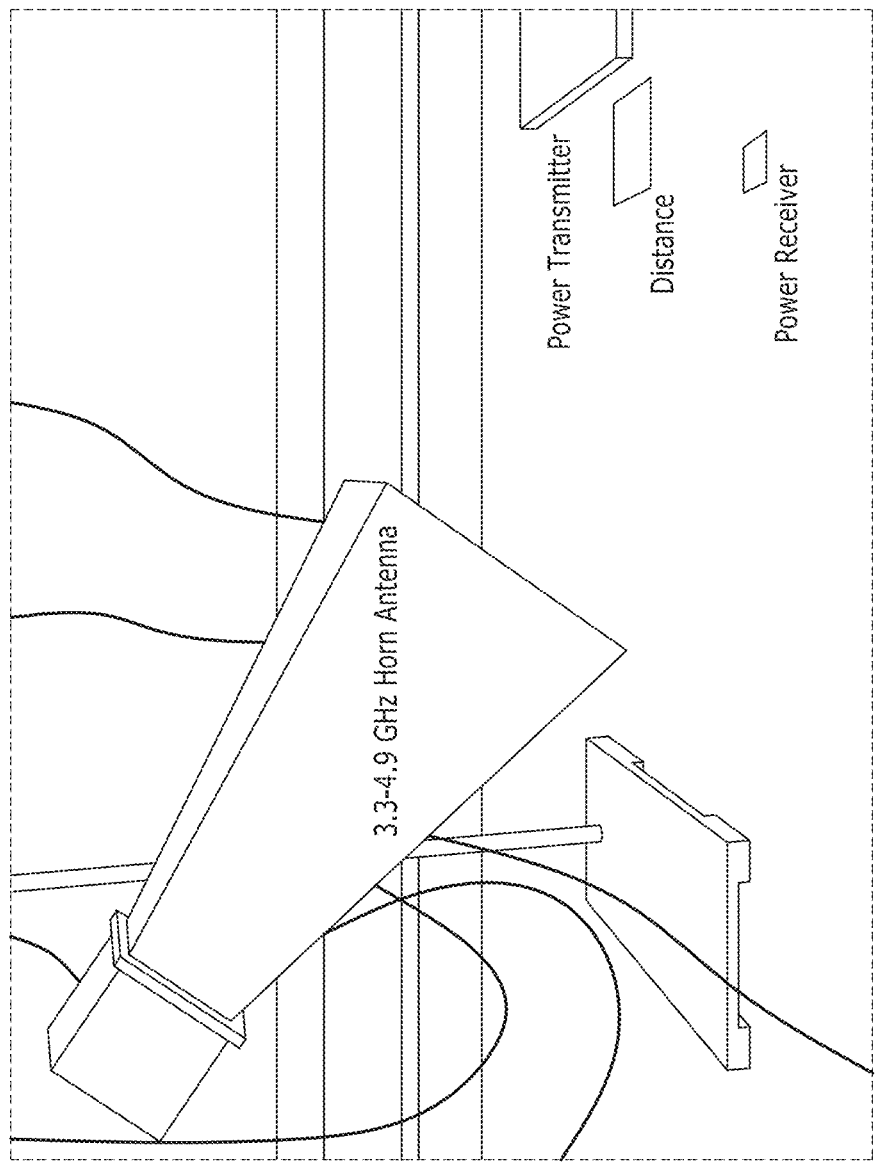
FIG. 17 illustrates a measurement setup in accordance with an embodiment of the invention.

The Tx and Rx coils as shown in FIG. 9 can be fabricated on FR4 laminates. The Tx coil can be matched to a 50-Ω signal source at 13.56 MHz. The power receiver can incorporate a simple monopole antenna of 12 mm length for IR-UWB back-telemetry. A horn antenna cascaded with a band-pass filter and a low-noise amplifier can be positioned 30 cm away as the back-telemetry receiver as shown in FIG. 17 in accordance with an embodiment of the invention.

Figure 18:
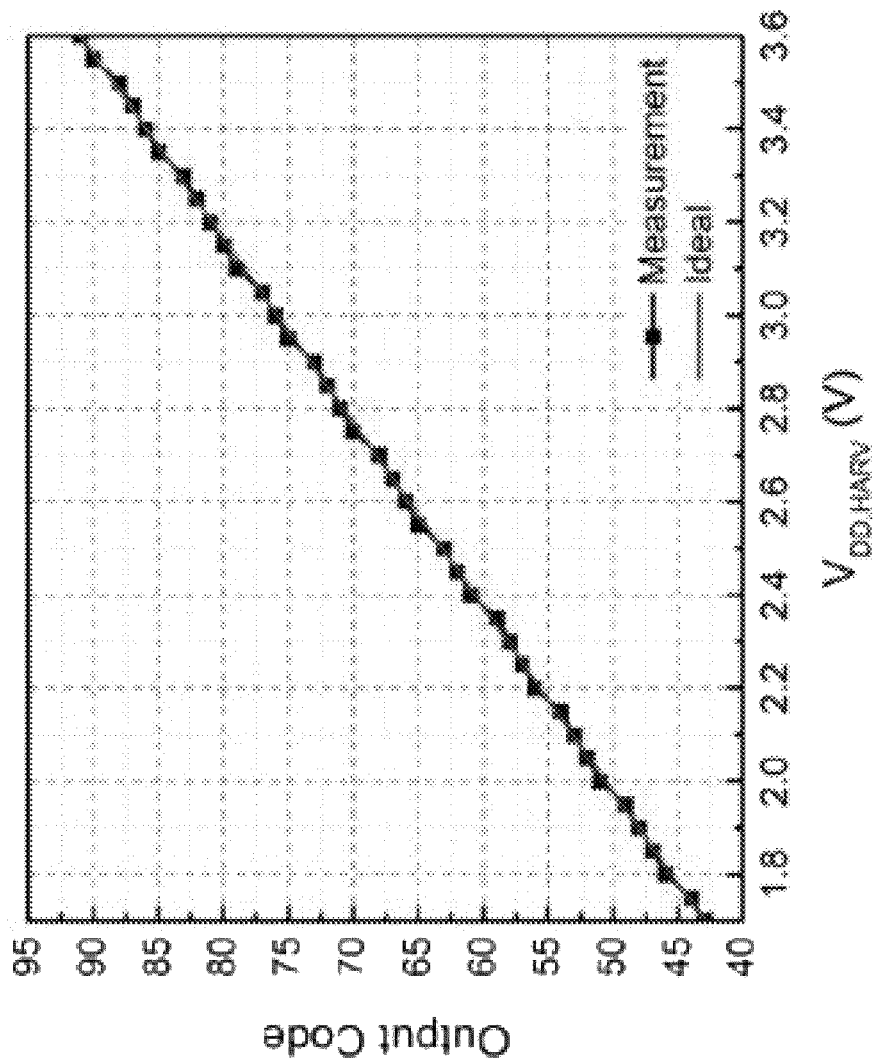
FIG. 18 illustrates wirelessly measured ADC output codes versus the harvested voltage in accordance with an embodiment of the invention.
Figure 19:
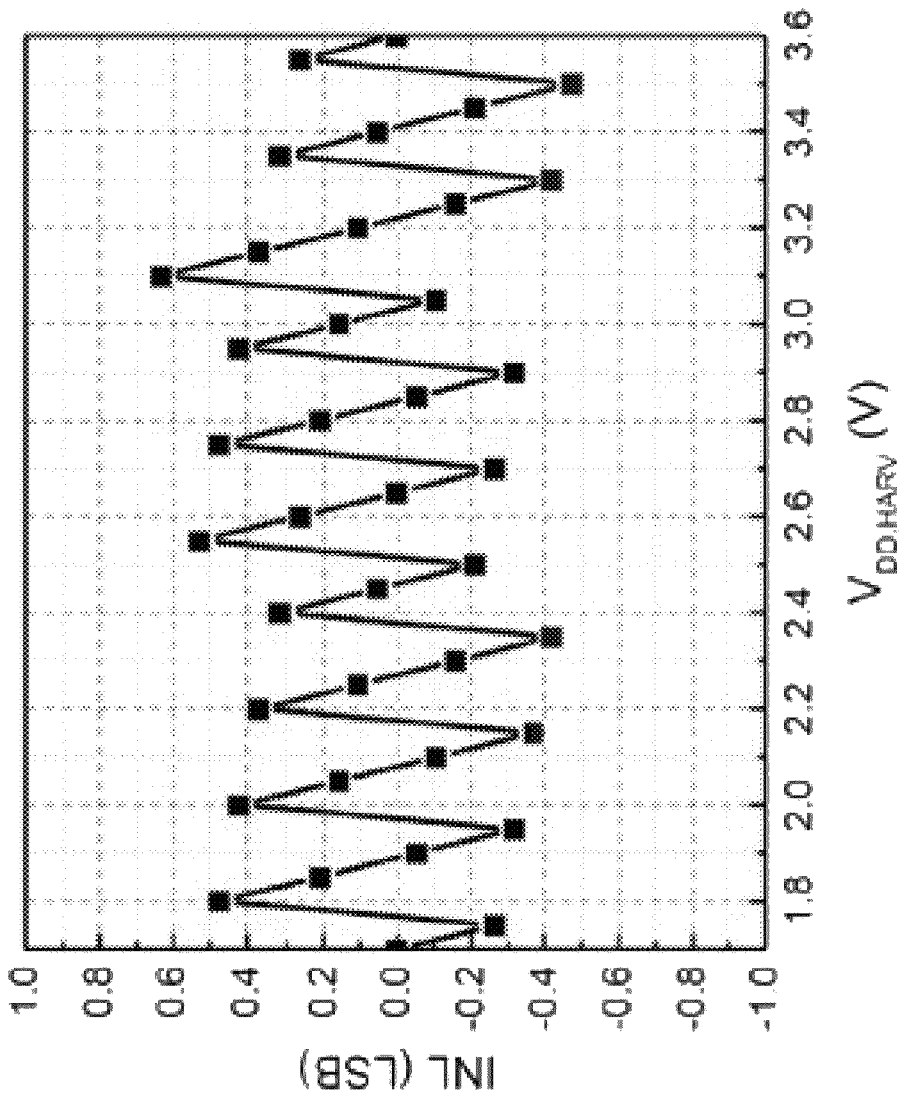
FIG. 19 illustrates INL of an ADC in accordance with an embodiment of the invention.

The ADC output versus the harvested voltage can be wirelessly measured with remarkable linearity as shown in FIG. 18 in accordance with an embodiment of the invention. The result also verifies the proper design of the auxiliary blocks such as the BGRs and the local LDO. The integral nonlinearity (INL), e.g., the discrepancy between the measurement codes and the ideal values (red line), is plotted in FIG. 19 in accordance with an embodiment of the invention, which rarely exceeds a half LSB.

Figure 20B:
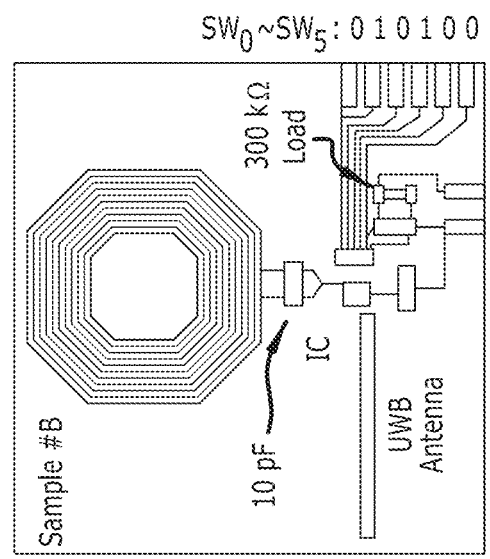
FIG. 20 illustrates pictures of sample (a) #A and (b) #B with #B incorporating an addition 10-pF parallel capacitor; #A and #B respectively adapt to capacitor bank codes, '100100' and '001010' in accordance with an embodiment of the invention.
Figure 20A:
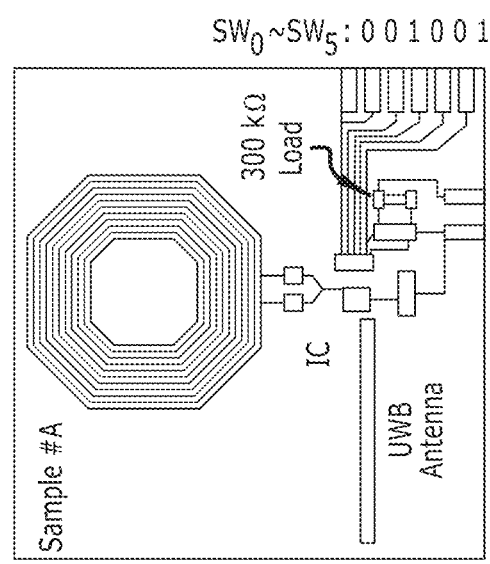

Two power receivers #A and #B can be assembled with #B incorporating an additional 10-pF parallel capacitor as shown in FIG. 20 in accordance with an embodiment of the invention. They can be used to drive a 300-kΩ resistor that manifests a typical tens-µW IMD. Upon wireless power onset, sample #A can automatically adapt $S_{W5}$~$S_{W0}$ to '100100', while #B adapts to '001010'. The code difference is 26 that corresponds to 9.9 pF as each switched capacitor unit contributes 380 fF. This result is remarkably close to the nominal value of the additional capacitor, 10 pF.

Figure 21:
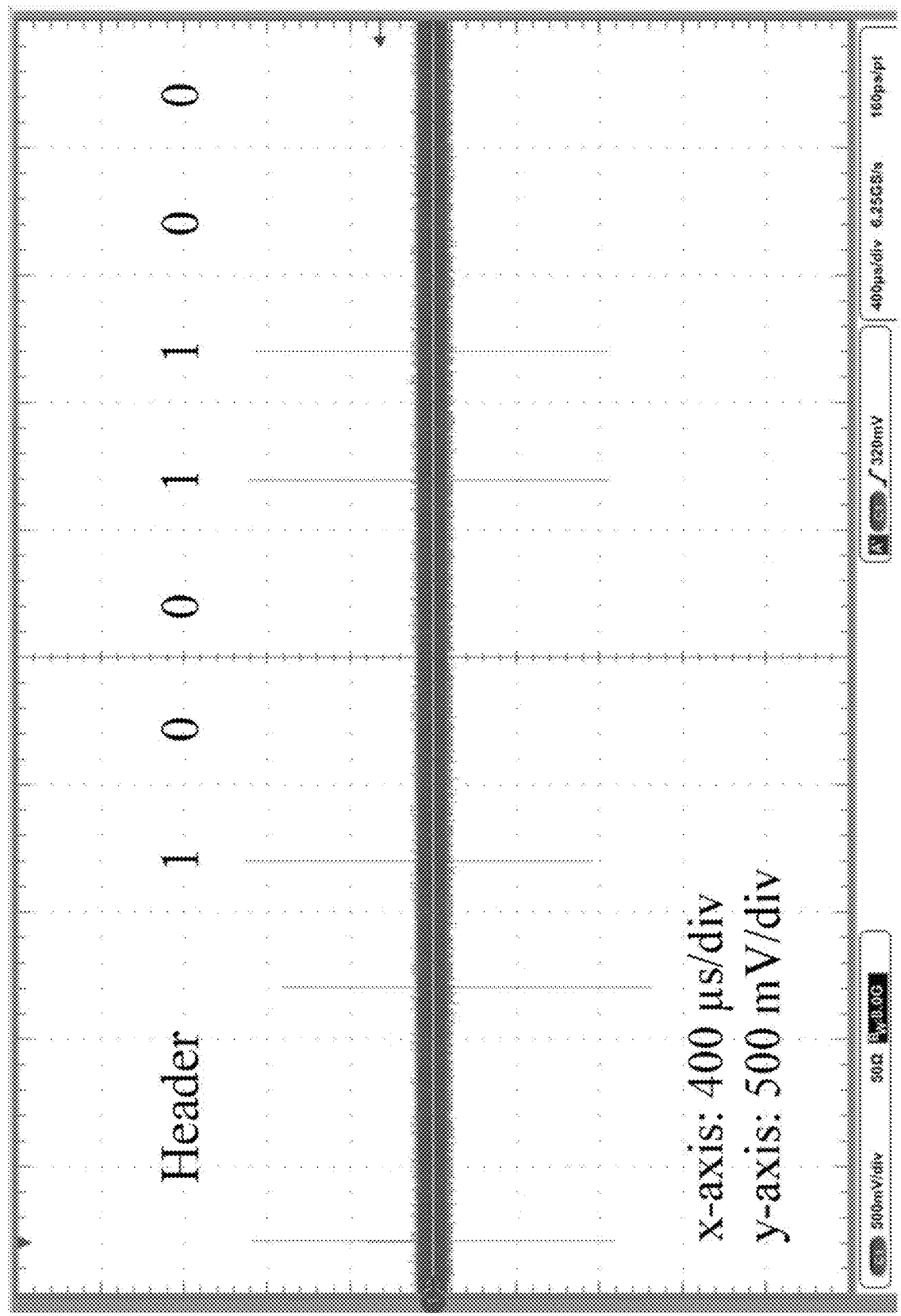
FIG. 21 illustrates transient waveform of an IR-UWB signal '1001100' in accordance with an embodiment of the invention.
Figure 22:
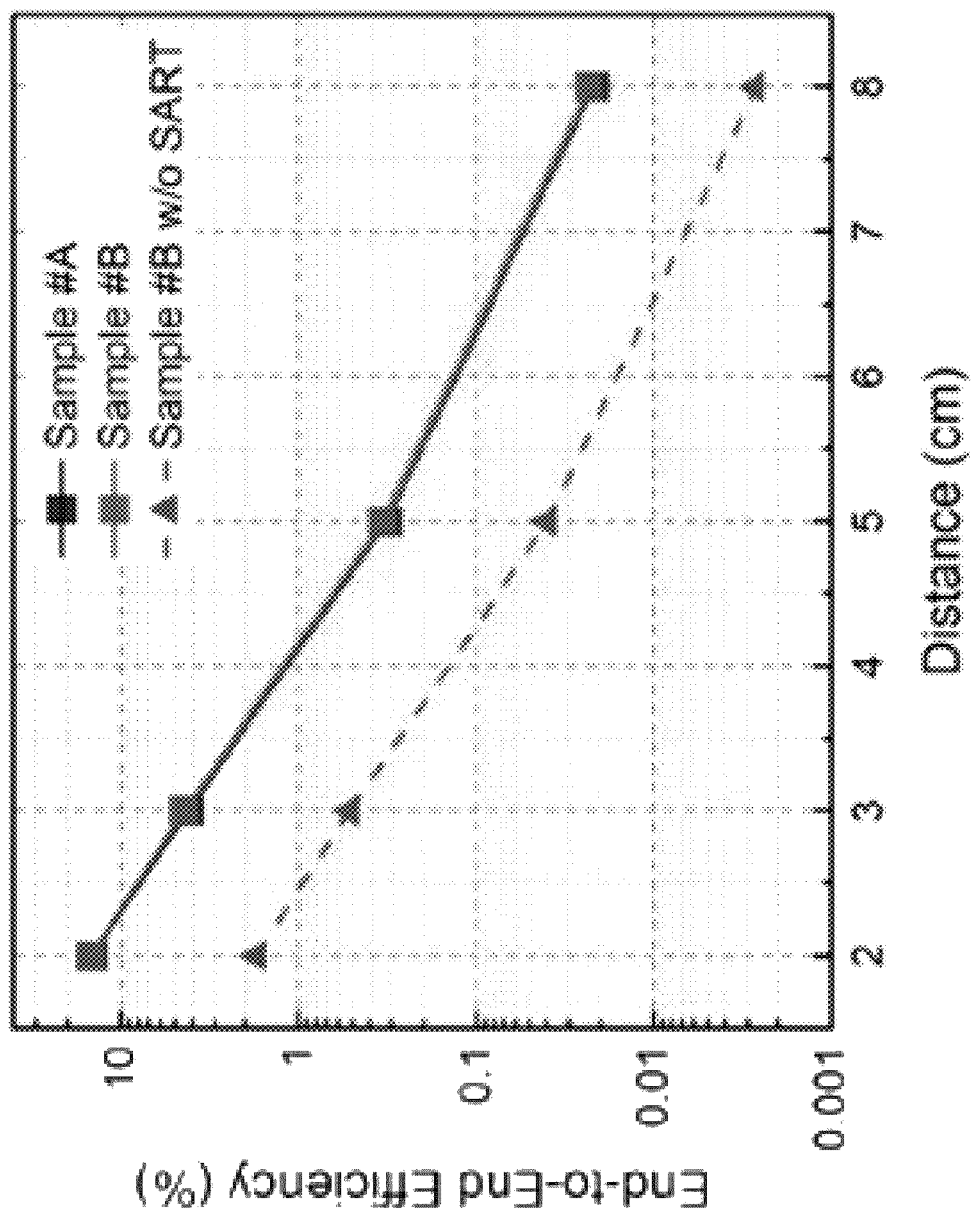
FIG. 22 illustrates end-to-end efficiency at different Tx-Rx distances for samples #A and #B and speculated results without SART in accordance with an embodiment of the invention.

The power transfer efficiency as a function of the Tx-Rx distance is investigated. The measurement is performed at the distances of 2 cm, 3 cm, 5 cm, and 8 cm. The Tx power is adjusted until the wireless reading shows '1001100' indicating an output voltage of 3 V as shown in FIG. 21 in accordance with an embodiment of the invention. The end-to-end efficiency can be calculated as the ratio between the load power, 30 µW, and the Tx power (as illustrated in FIG. 22). At 2 cm, the overall link efficiency reaches as high as 16.1%. The efficiencies for samples #A and #B are remarkably close with a discrepancy of less than 10%.

Figure 23:
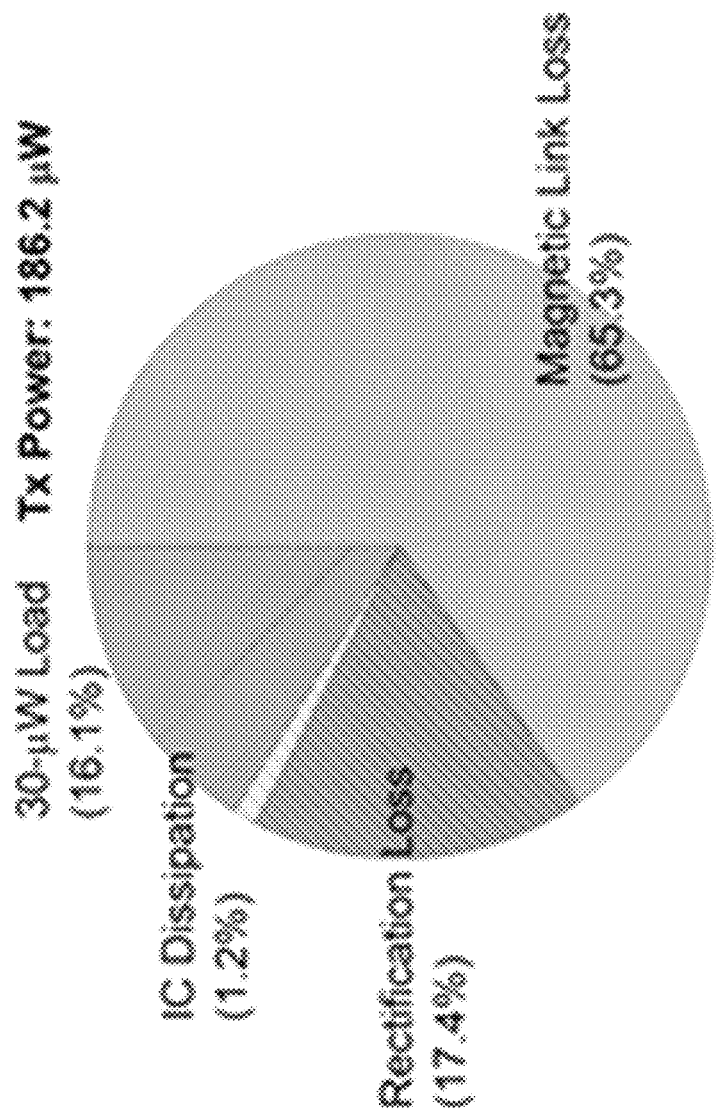
FIG. 23 illustrates a breakdown of power in a 2-cm power transfer link given the Tx power of 186.2 µW.

Since the rectification and loading efficiencies equal 49.9% and 93.02% (10/10.75), respectively, the inductive coupling efficiency as the theoretical power transfer limit can be speculated and plotted in FIG. 22 in accordance with an embodiment of the invention. The power breakdown of the 2-cm scenario given the Tx power of 186.2 µW is shown in FIG. 23 in accordance with an embodiment of the invention.

The input impedance of the rectifier can be simulated to incorporated a parallel resistor of 3.27 kΩ. Therefore, considering the inductance of the Rx coil, the quality factor of the front-end tank approximately equals 6. Without resonance compensation, a capacitor offset of 10 pF would degrade the link efficiency by 89% according to simulations in FIG. 10 in accordance with an embodiment of the invention. The speculated result without SART is also plotted in FIG. 22 in accordance with an embodiment of the invention.

Figure 24:
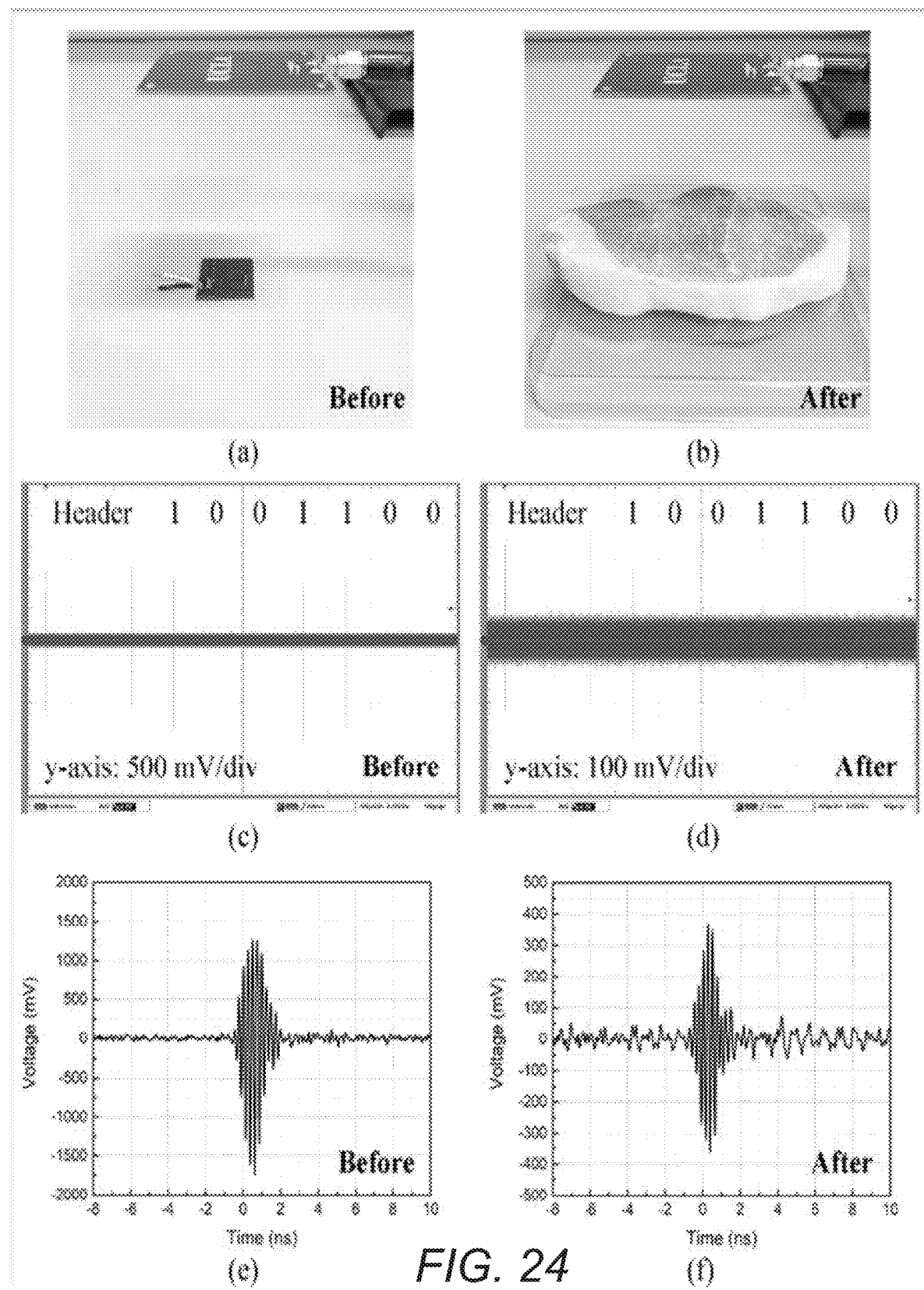
FIG. 24 illustrates in vitro experiment with a piece of pork loin covering the power receiver (a) Before and (b) after the pork loin covering the device, The corresponding transient waveforms of the IR-UWB signals are shown in (c, e) and (d, f), respectively, the IR-UWB data maintains the same with and without the pork loin in accordance with an embodiment of the invention.

A piece of 1.5-cm thick pork loin is used to entirely cover the power receiver to verify the operation of the inductive coupling and IR-UWB data links as shown in FIG. 24 in accordance with an embodiment of the invention. Particularly, while the IR-UWB signal shows a weakened swing due to tissue losses (FIG. 24(c-f)), the power transfer link efficiency does not change at all, which is manifested by the unchanged harvested voltage. It is consistent with the nature of magnetic coupling. The feature was also verified in a vivo experiment in which induction-based power transfer was demonstrated through a porcine model's chest.

Figure 25:
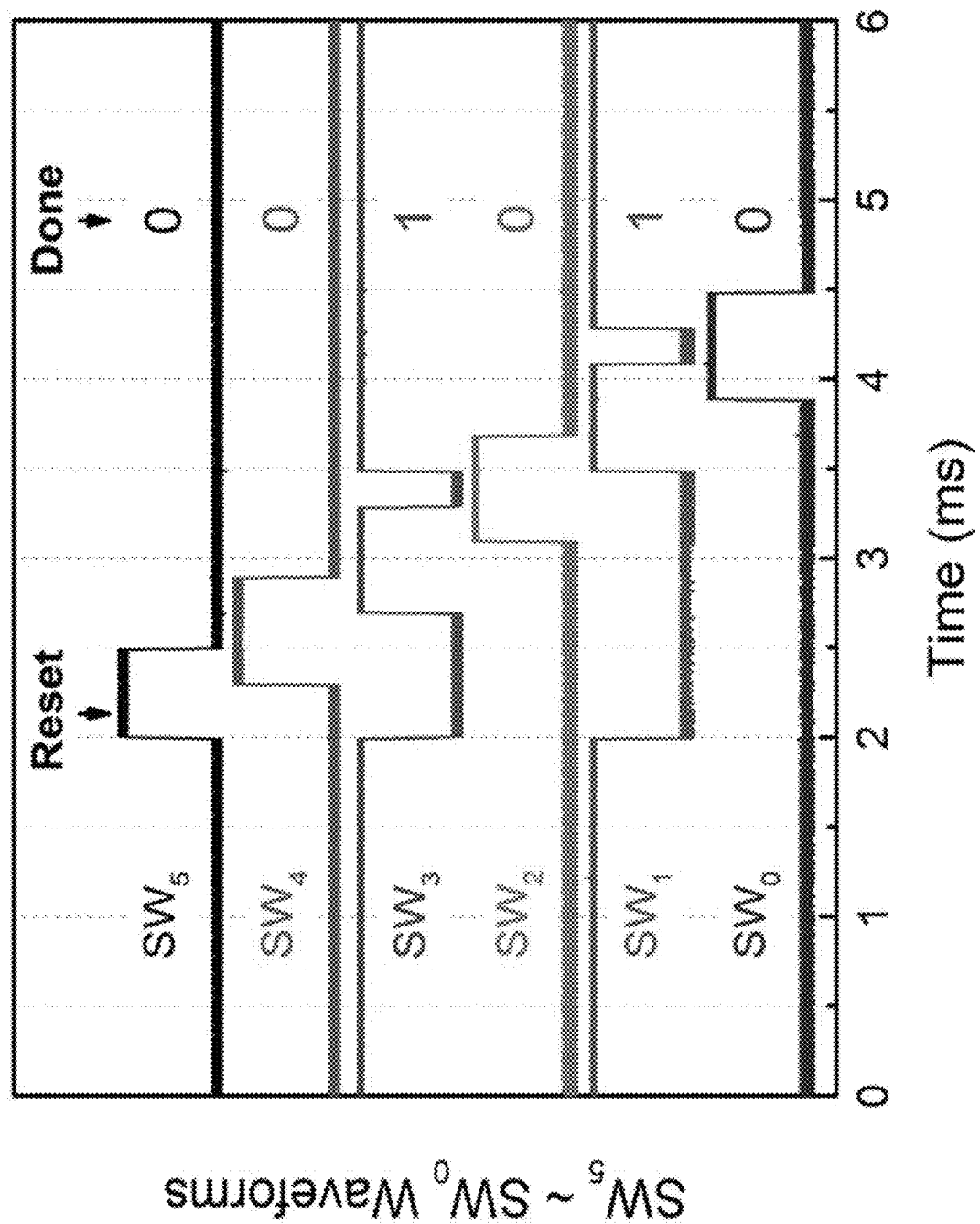
FIG. 25 illustrates measured resonance compensation logic waveforms during adaptation in accordance with an embodiment of the invention.
Figure 26B:
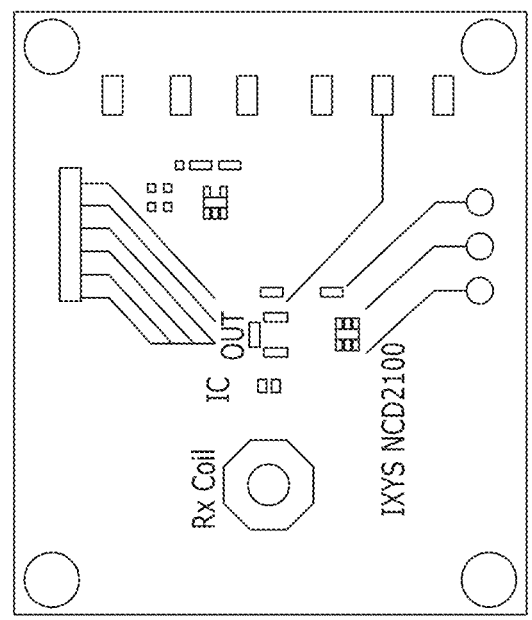
FIG. 26 illustrates power receiver incorporating a digitally controlled capacitor at the energy-harvesting front-end, (a) Photo of the printed circuit board housing the proposed IC, Rx coil, and the digitally controlled capacitor, NCD2100, (b) Overall setup in which a microcontroller is used to program the capacitor and retrieve data from the IC in accordance with an embodiment of the invention.
Figure 26A:
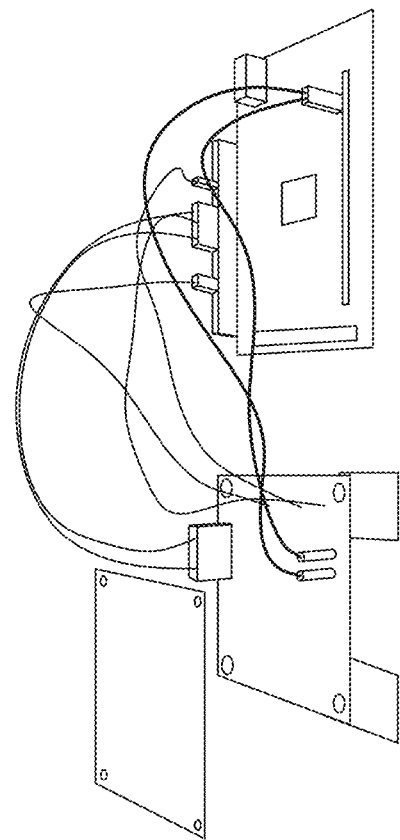
Figure 27:
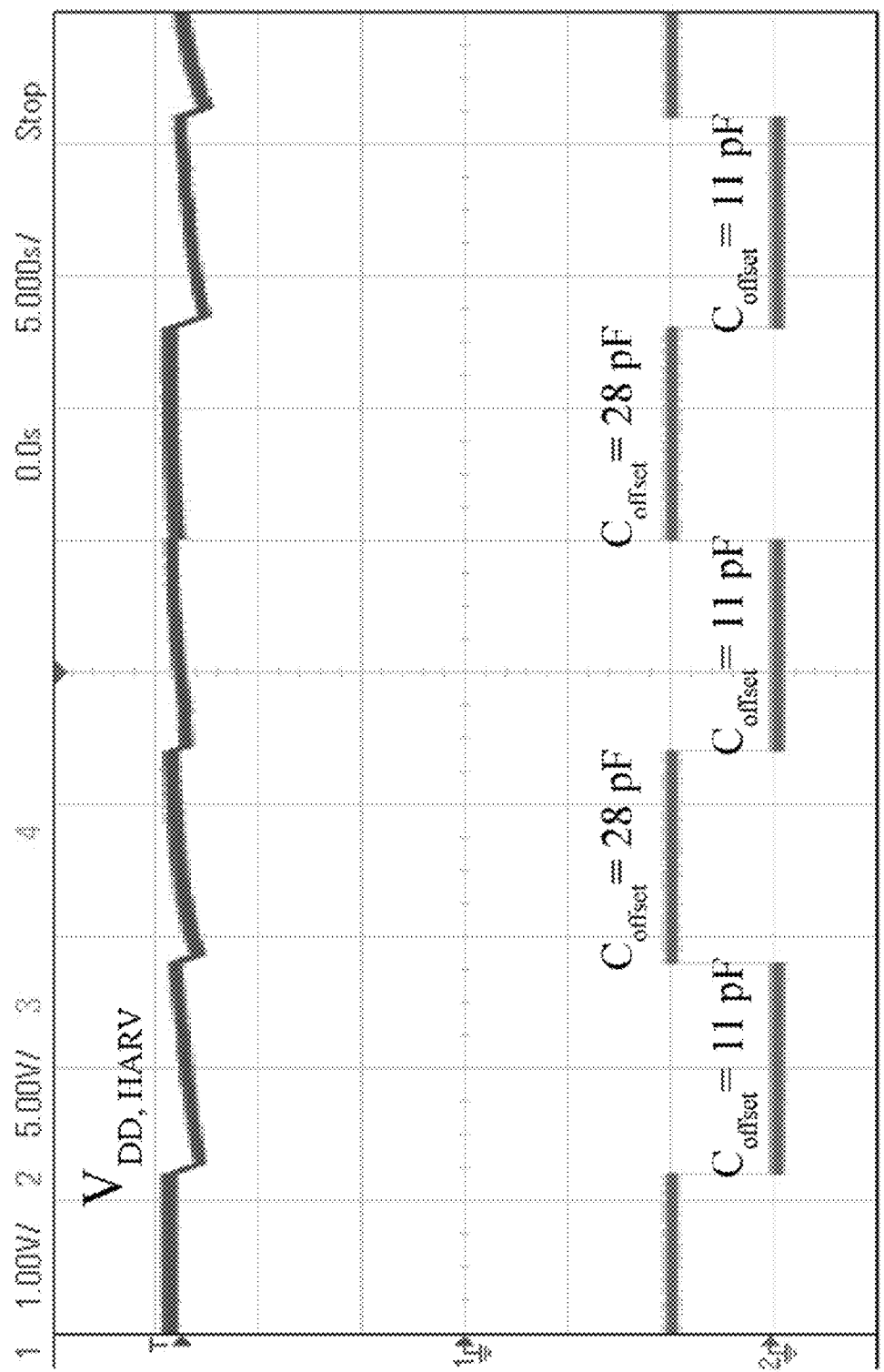
FIG. 27 illustrates Output voltage waveform in response to transient resonance capacitor offsets in accordance with an embodiment of the invention.

Exemplary waveforms of the $S_{W5}$~$S_{W0}$ adaptation are demonstrated in FIG. 25 in accordance with an embodiment of the invention. Once SART is executed, the convergence only takes 12 clock cycles or 2.4 ms. The response of the power receiver to transient resonance capacitor offsets is measured with the assist of an off-the-shelf digitally controlled capacitor, IXYS NCD2100, that is connected in parallel at the front-end, as illustrated in FIG. 26 in accordance with an embodiment of the invention. The output node of the power receiver connects the load resistor of 300 kΩ and a decoupling capacitor of 47 pF. The capacitor offset is changed between 11 pF and 28 pF every 8 s and the output waveform is shown in FIG. 27 in accordance with an embodiment of the invention. While a voltage droop occurs with each switching, the output voltage will resume a close value. The recovery time is dependent on the decoupling capacitance.

Figure 28:
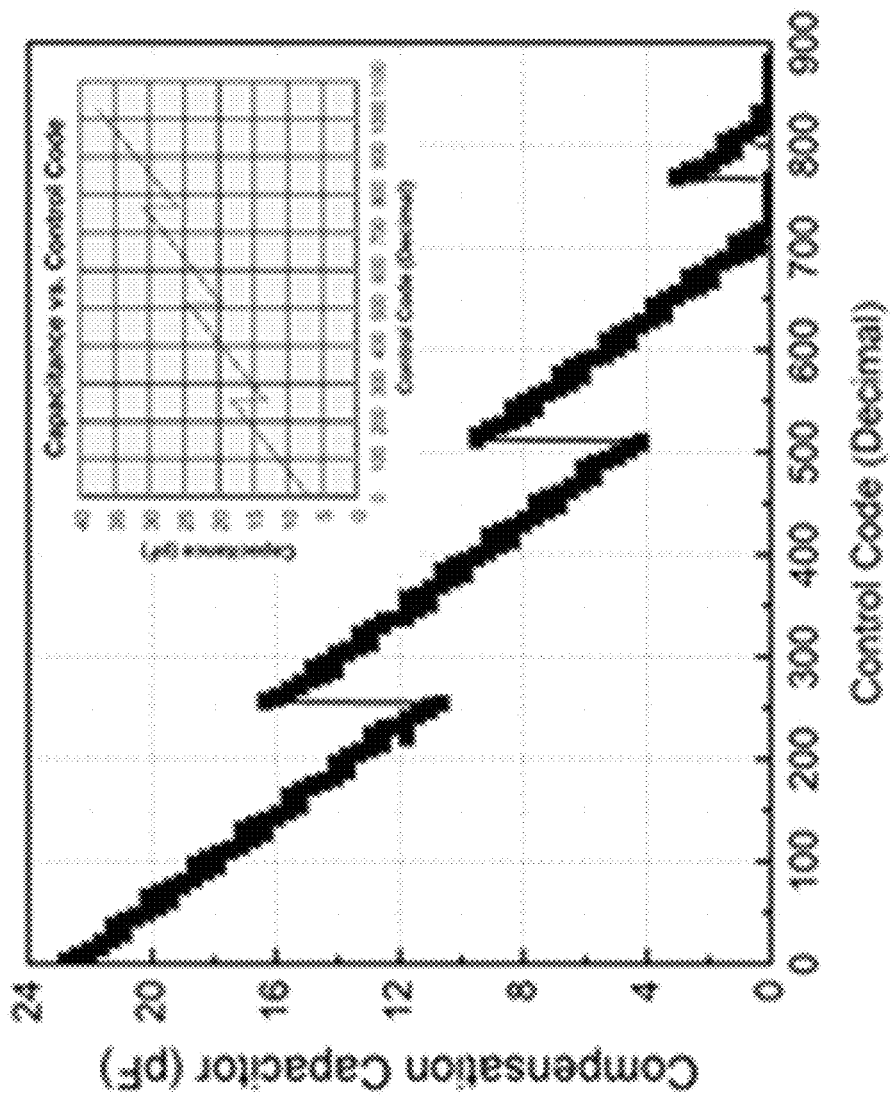
FIG. 28 illustrates compensation capacitor of the IC adapted to the capacitance of NCD2100, the inset shows the NCD2100 capacitance as a function of the control code according to its datasheet in accordance with an embodiment of the invention.
Figure 29:
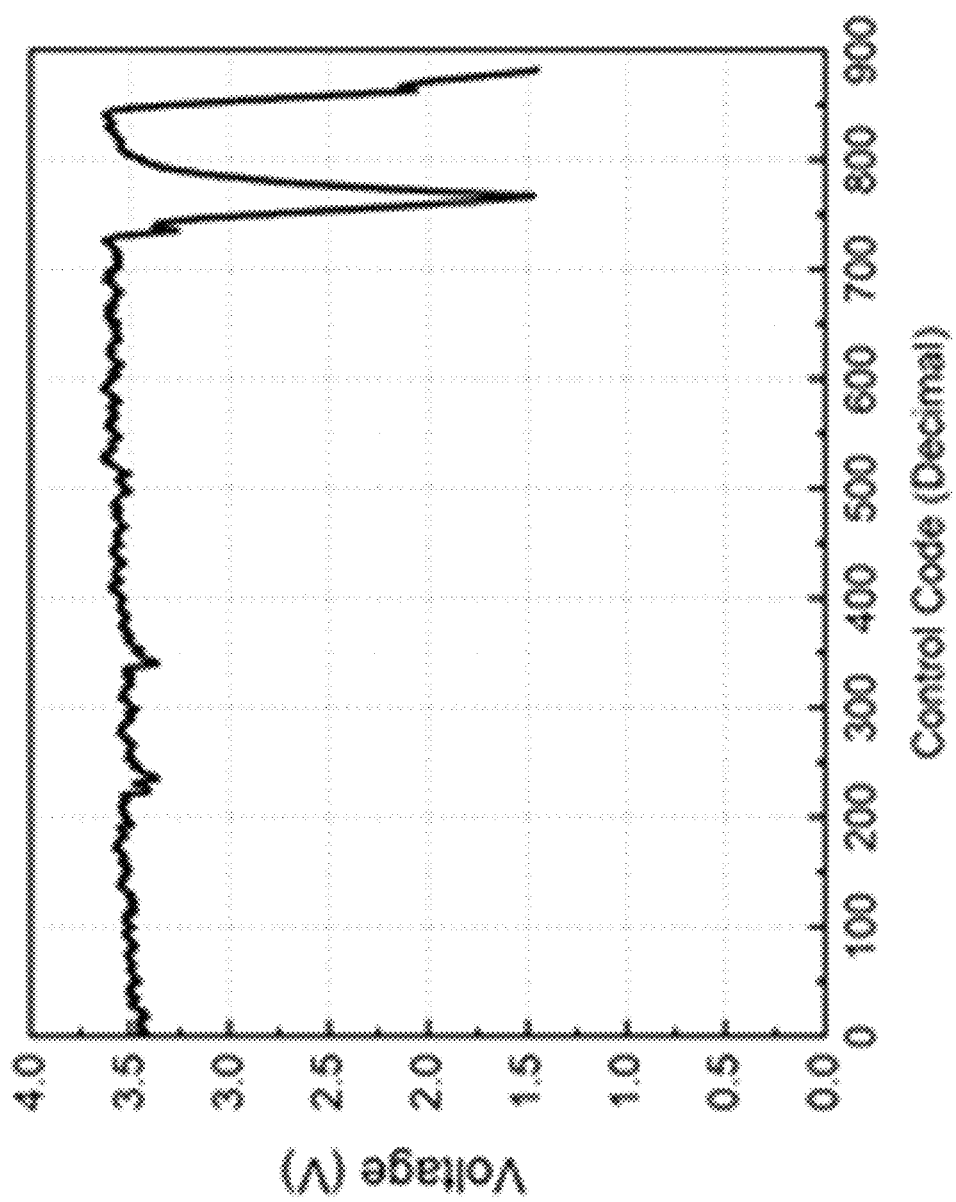
FIG. 29 illustrates generated output voltage at each control code of NCD2100 in accordance with an embodiment of the invention.

The capacitance of NCD2100 is swept in its full range. 6.6 pF to 37.553 pF is covered with 10 control bits including course and fine bits. The capacitance as a function of the control code is demonstrated in the inset of FIG. 28 in accordance with an embodiment of the invention according to its datasheet. The dependence is not entirely linear. Measurement shows that the IC accurately compensates for the offset in its full dynamic range as shown in FIG. 28 in accordance with an embodiment of the invention. The output voltage stays relatively stable for the resonance capacitor offset from 6.6 pF to about 29 pF as shown in FIG. 29 in accordance with an embodiment of the invention, which corresponds to the self-resonant frequency of the Rx tank up to about 26.5 MHz. Small fluctuations exist as the system's operation is based on discrete compensation capacitance values. Only when the capacitor offset is out of the compensation range, will there exhibit a dramatic drop of the output voltage.

The resonance compensation technique in accordance with many embodiments of the system is compared with the prior art as summarized in Table II in FIG. 30 and FIG. 31. The SART technique in accordance with many embodiments of the invention is time- and energy-efficient, and, therefore, not only addresses one-time calibration but offers the real-time adaptability to ever-changing dielectric environments and loading conditions. State-of-the-art inductive power receivers for low-power IMDs are further compared in Table III. Accordingly, many embodiments feature the lowest input power sensitivity making it particularly suitable for powering ultra-low-power IMDs. An end-to-end efficiency of about 16% is achieved regardless of a 10-pF capacitor offset when driving a 30-μW load. Since a high power transfer efficiency is increasingly more challenging for lighter loads, the efficiency normalized to the corresponding load is considered.

Although specific implementations for an inductive power receiver and sensors with real-time resonance adaptation and wireless voltage regulation are discussed above with respect to FIGS. 1-31, any of a variety of implementations utilizing the above discussed techniques can be utilized for a power receiver and/or sensors in accordance with embodiments of the invention. While the above description contains many specific embodiments of the invention, these should not be construed as limitations on the scope of the invention, but rather as an example of one embodiment thereof. It is therefore to be understood that the present invention may be practice otherwise than specifically described, without departing from the scope and spirit of the present invention. Thus, embodiments of the present invention should be considered in all respects as illustrative and not restrictive.

What is claimed is:

1. A power receiver system, comprising:
an inductive coil configured to receive wireless power from an external transmitter;
a resonance capacitor comprising a capacitor bank having an input coupled to the inductive coil, and a plurality of capacitors configured to be selectively included in one or more of a plurality of capacitor-bank settings;
a power-receiving frontend RF-DC rectifier coupled to the capacitor bank; and
an amplitude detector having an input coupled to the input of the capacitor bank and an output, the amplitude detector configured to provide measurements of the input of the capacitor bank, and
a resonance compensator having outputs coupled to the capacitor bank and an input coupled to the output of the amplitude detector, the resonance compensator configured to:
sample the measurements of the input of the capacitor bank through the amplitude detector; and
adapt the resonance capacitor by selecting an optimal capacitor-bank setting based on the measurements of the input of the capacitor bank in real-time to adapt to changes on the inductive coil.

2. The power receiver system of claim 1, wherein the power-receiving frontend RF-DC rectifier comprises a Dickson-stage passive rectifier and the capacitor bank comprises a binary-weighted capacitor bank implemented in parallel with the Dickson-stage passive rectifier.

3. The power receiver system of claim 1, wherein the measurements of the input of the capacitor bank are in the analog domain.

4. The power receiver system of claim 1, wherein the capacitor bank is a 6-bit capacitor bank and the resonance compensator is configured to periodically adapt the resonance capacitor based on the measurements of the input of the capacitor bank using a successive-approximation-resonance-tuning process.

5. The power receiver system of claim 1, wherein the resonance compensator is configured to adapt the resonance capacitor a plurality of times per second.

6. The power receiver system of claim 1, wherein the resonance compensator comprises:
latch circuitry having an output and a plurality of inputs, wherein the latch circuitry is configured to output a swing measurement corresponding to a change in the output of the amplitude detector due to a change in capacitor-bank setting, and
logic circuitry coupled to the output of the latch circuitry.

7. The power receiver system of claim 6, wherein the resonance compensator is configured to select an optimal capacitor-bank setting by being further configured to:
obtain a plurality of swing measurements,
identify a maximum swing measurement from the plurality of swing measurements, and
select the capacitor-bank setting associated with the maximum swing measurement as the optimal capacitor-bank setting.

8. The power receiver system of claim 6, wherein the resonance compensator further comprises a plurality of hold capacitors, each selectively coupled to the output of the amplitude detector,
wherein each of the plurality of inputs of the latch circuitry is selectively coupled to a respective one of the plurality of hold capacitors.

9. The power receiver system of claim 6, wherein the change in capacitor-bank settings comprises a change from a first capacitor-bank setting to a second capacitor-bank setting that is consecutive in time with the first capacitor-bank setting.

10. The power receiver system of claim 1, wherein the resonance capacitor is characterized by an offset, and an impedance of the inductive coil is approximately symmetric against the offset.

11. The power receiver system of claim 1, further comprising a transmitter configured to transmits information to an external controller.

12. The power receiver system of claim 11, wherein:
the information comprises a real-time harvested voltage reading,
the transmitter is an ultra-wideband impulse radio (IR-UWB) transmitter as a back telemetry for output voltage regulation, and
an output voltage from the IR-UWB transmitter is regulated based on back telemetry transmitting the real-time harvested voltage reading.

13. The power receiver system of claim 1, further comprising:
a coarse bandgap reference (BGR-course) and a local low-dropout regulator (LDO) coupled to the output of the power-receiving frontend RF-DC rectifier and that generates a voltage supply for circuitry; and
a fine bandgap reference (BGR-fine) coupled to the output of the LDO and that generates a stable voltage reference.

14. A wirelessly powered sensor chip configured for placement relative to a surrounding environment, comprising:
an inductive coil configured to receives wireless power from an external transmitter;
a capacitor bank having an input coupled to the inductive coil, the capacitor bank comprising a plurality of capacitors configured to be selectively included in one or more of a plurality of capacitor-bank settings;
a power-receiving frontend RF-DC rectifier coupled between the capacitor bank; and
an amplitude detector having an input coupled to the input of the capacitor bank and an output, the amplitude detector configured to provide measurements of the input of the capacitor bank, and
a resonance compensator having outputs coupled to the capacitor bank and an input coupled to the output of the amplitude detector, the resonance compensator configured to:
sample the measurements of the input of the capacitor bank through the amplitude detector;
select an optimal capacitor-bank setting based on the measurements of the input of the capacitor bank in real-time to adapt to the surrounding environment; and
a transmitter configured to transmit information related to the capacitor-bank settings and voltage readings to an external controller.

15. The wirelessly powered sensor chip of claim 14, further comprising:
an analog-to-digital convertor having an input coupled to the output of the power-receiving frontend RF-DC rectifier, and an output, wherein the analog-to-digital convertor is configured to provide the voltage readings; and
a serializer and packetizer having an input coupled to the output of the analog-to-digital convertor, and an output coupled to the transmitter,
wherein operations of the resonance compensator, the analog-to-digital convertor, and the serializer and packetizer are duty cycled.

16. The wirelessly powered sensor chip of claim 15, wherein operations of the resonance compensator, the analog-to-digital convertor, and the serializer and packetizer occur a plurality of time per second.

17. The wirelessly powered sensor chip of claim 14, wherein the capacitor-bank settings are used by the external controller to determine a type of material in the surrounding environment.

18. The wirelessly powered sensor chip of claim 14, wherein changes to the capacitor-bank settings and are used by the external controller to detect near-field changes in the surrounding environment.

19. The wirelessly powered sensor chip of claim 14, wherein changes to a voltage reading without changes to the capacitor-bank settings are used by the external controller to detect far-field changes in the surrounding environment.

20. The wirelessly powered sensor chip of claim 14, wherein the capacitor bank is a 6-bit capacitor bank and the resonance compensator is configured to periodically adapt the capacitor bank based on the measurements of the input of the capacitor bank using a successive-approximation-resonance-tuning process.

21. The wirelessly powered sensor chip of claim 14, wherein the resonance compensator comprises:
latch circuitry having an output and a plurality of inputs, wherein the latch circuitry is configured to output a swing measurement corresponding to a change in the output of the amplitude detector due to a change in capacitor-bank setting, and
logic circuitry coupled to the output of the latch circuitry.

22. The wirelessly powered sensor chip of claim 14, wherein the capacitor bank is characterized by an offset, and an impedance of the inductive coil is approximately symmetric against the offset.

23. The wirelessly powered sensor chip of claim 14, wherein:
the information comprises a real-time harvested voltage reading,
the transmitter is an ultra-wideband impulse radio (IR-UWB) transmitter as a back telemetry for output voltage regulation, and
an output voltage from the IR-UWB transmitter is regulated based on back telemetry transmitting the real-time harvested voltage reading.

24. A sensor system comprising:
a wirelessly powered sensor chip configured for placement relative to a surrounding environment, comprising:
an inductive coil configured to receives wireless power from an external transmitter;
a capacitor bank having an input coupled to the inductive coil, the capacitor bank comprising a plurality of capacitors configured to be selectively included in one or more of a plurality of capacitor-bank settings;
a power-receiving frontend RF-DC rectifier coupled between the capacitor bank; and
an amplitude detector having an input coupled to the input of the capacitor bank and an output, the amplitude detector configured to provide measurements of the input of the capacitor bank, and
a resonance compensator having outputs coupled to the capacitor bank and an input coupled to the output of the amplitude detector, the resonance compensator configured to:
sample the measurements of the input of the capacitor bank through the amplitude detector, and select an optimal capacitor-bank setting based on the measurements of the input of the capacitor bank in real-time to adapt to the surrounding environment;
a transmitter configured to transmit information related to the capacitor-bank settings and voltage readings; and
a controller configured to receive and process the transmit information related to the capacitor-bank settings and voltage readings to determine as aspect of the surrounding environment.

25. The sensor system of claim 24, wherein the controller is configured to determine a type of material in the surrounding environment based on the capacitor-bank settings.

26. The sensor system of claim 24, wherein the controller is configured to detect near-field changes in the surrounding environment based on changes to the capacitor-bank settings.

27. The sensor system of claim 24, wherein the controller is configured to detect far-field changes in the surrounding environment based on changes to a voltage reading without changes to the capacitor-bank settings.

* * * * *